United States Patent
Sanchez Valente et al.

(10) Patent No.: US 9,409,156 B2
(45) Date of Patent: Aug. 9, 2016

(54) OXIDATIVE DEHYDROGENATION OF ETHANE TO ETHYLENE AND PREPARATION OF MULTIMETALLIC MIXED OXIDE CATALYST FOR SUCH PROCESS

(71) Applicants: Jaime Sanchez Valente, Mexico City (MX); Jose Manuel Lopez Nieto, Valencia (ES); Hector Armendariz Herrera, Mexico City (MX); Amada Masso Ramirez, Valencia (ES); Francisco Ivars Barcelo, Valencia (ES); Maria de Lourdes Alejandra Guzman Castillo, Mexico City (MX); Roberto Quintana Solorzano, Mexico City (MX); Andrea Rodriguez Hernandez, Mexico City (MX); Paz Del Angel Vicente, Mexico City (MX); Etel Maya Flores, Mexico City (MX)

(72) Inventors: Jaime Sanchez Valente, Mexico City (MX); Jose Manuel Lopez Nieto, Valencia (ES); Hector Armendariz Herrera, Mexico City (MX); Amada Masso Ramirez, Valencia (ES); Francisco Ivars Barcelo, Valencia (ES); Maria de Lourdes Alejandra Guzman Castillo, Mexico City (MX); Roberto Quintana Solorzano, Mexico City (MX); Andrea Rodriguez Hernandez, Mexico City (MX); Paz Del Angel Vicente, Mexico City (MX); Etel Maya Flores, Mexico City (MX)

(73) Assignees: Instituto Mexicano Del Petroleo, Mexico City (MX); Pemex Petroquimica, Veracruz (MX); Universidad Politecnica De Valencia, Valencia (ES)

( * ) Notice: Subject to any disclaimer, the term of this patent is extended or adjusted under 35 U.S.C. 154(b) by 0 days.

(21) Appl. No.: 13/655,620

(22) Filed: Oct. 19, 2012

(65) Prior Publication Data
US 2014/0114109 A1    Apr. 24, 2014

(51) Int. Cl.
C07C 5/48    (2006.01)
B01J 23/28   (2006.01)
(Continued)

(52) U.S. Cl.
CPC ............. *B01J 23/8877* (2013.01); *B01J 23/28* (2013.01); *B01J 23/30* (2013.01); *B01J 23/885* (2013.01);
(Continued)

(58) Field of Classification Search
USPC .......................................... 585/658; 502/312
See application file for complete search history.

(56) References Cited

U.S. PATENT DOCUMENTS 4,250,346 A     2/1981  Young et al.
4,524,236 A  *  6/1985  McCain ................. 585/658
(Continued)

FOREIGN PATENT DOCUMENTS

CN    102176966    9/2011
EP    0294845      12/1988
(Continued)

OTHER PUBLICATIONS

Watanabe et al., 2006, Comparative study on the catalytic performance of single-phase MO-V-O-based metal oxide catalysts in propane ammoxidation to acrylonitrile, Ind. Eng. Chem. Res., vol. 45, pp. 607-614.*
(Continued)

*Primary Examiner* — In Suk Bullock
*Assistant Examiner* — Youngsul Jeong
(74) *Attorney, Agent, or Firm* — Dickinson Wright PLLC

(57) ABSTRACT

Oxidative dehydrogenation of light paraffins, such as ethane at moderate temperatures (<500° C.) to produce ethylene without the formation of side products such as acetic acid and/or other oxygenated hydrocarbons is achieved using tellurium-free, multimetallic catalysts possessing orthorhombic M1 phase and other crystalline structures that have an important role for obtaining high performance catalysts for the oxidative dehydrogenation of ethane to ethylene. Such catalysts are prepared using thermal and hydrothermal methods.

14 Claims, 18 Drawing Sheets

(51) Int. Cl.

| | | |
|---|---|---|
| *B01J 23/30* | (2006.01) | |
| *B01J 23/887* | (2006.01) | |
| *B01J 37/08* | (2006.01) | |
| *B01J 37/10* | (2006.01) | |
| *B01J 35/00* | (2006.01) | |
| *B01J 37/00* | (2006.01) | |
| *B01J 23/885* | (2006.01) | |
| *B01J 37/12* | (2006.01) | |

(52) U.S. Cl.
CPC ............ *B01J 35/004* (2013.01); *B01J 37/0018* (2013.01); *B01J 37/08* (2013.01); *B01J 37/10* (2013.01); *B01J 37/12* (2013.01); *C07C 5/48* (2013.01); *B01J 2523/00* (2013.01); *C07C 2521/06* (2013.01); *C07C 2523/04* (2013.01); *C07C 2523/08* (2013.01); *C07C 2523/10* (2013.01); *C07C 2523/14* (2013.01); *C07C 2523/18* (2013.01); *C07C 2523/20* (2013.01); *C07C 2523/22* (2013.01); *C07C 2523/26* (2013.01); *C07C 2523/28* (2013.01); *C07C 2523/30* (2013.01); *C07C 2523/72* (2013.01); *C07C 2523/745* (2013.01); *C07C 2523/75* (2013.01); *C07C 2523/755* (2013.01); *C07C 2523/887* (2013.01); *Y02P 20/52* (2015.11)

(56) References Cited

U.S. PATENT DOCUMENTS

| | | | |
|---|---|---|---|
| 4,568,790 | A | 2/1986 | McCain |
| 5,162,578 | A | 11/1992 | McCain, Jr. et al. |
| 5,821,192 | A | 10/1998 | Seely et al. |
| 5,994,580 | A | 11/1999 | Takahashi et al. |
| 6,030,920 | A | 2/2000 | Karim et al. |
| 6,060,422 | A | 5/2000 | Takahashi et al. |
| 6,194,610 | B1 | 2/2001 | Borchert et al. |
| 6,310,241 | B1 | 10/2001 | Karim et al. |
| 6,346,647 | B2 | 2/2002 | Tu et al. |
| 6,383,977 | B1 | 5/2002 | Karim et al. |
| 6,436,871 | B1 | 8/2002 | Liu |
| 6,514,902 | B1 | 2/2003 | Inoue et al. |
| 6,610,629 | B2 | 8/2003 | Hinago et al. |
| 6,777,571 | B2 | 8/2004 | Chaturvedi et al. |
| 6,864,384 | B2 | 3/2005 | Brazdil et al. |
| 7,109,144 | B2 | 9/2006 | Hinago et al. |
| 7,304,014 | B2 | 12/2007 | Cavalcanti et al. |
| 7,319,179 | B2 | 1/2008 | Lopez Nieto et al. |
| 8,105,971 | B2 | 1/2012 | Gaffney et al. |
| 2003/0100794 | A1 | 5/2003 | Karim et al. |
| 2005/0239643 | A1 | 10/2005 | Benderly et al. |
| 2006/0183941 | A1 | 8/2006 | Dubois et al. |
| 2008/0161602 | A1 | 7/2008 | Wang et al. |
| 2008/0194871 | A1* | 8/2008 | Dubois et al. .................. 562/549 |
| 2008/0248947 | A1 | 10/2008 | Zajac et al. |
| 2010/0256432 | A1 | 10/2010 | Arnold et al. |
| 2011/0245562 | A1 | 10/2011 | Kustov et al. |
| 2011/0245571 | A1 | 10/2011 | Kustov et al. |
| 2012/0016171 | A1 | 1/2012 | Kustov et al. |

FOREIGN PATENT DOCUMENTS

| | | |
|---|---|---|
| EP | 0294846 | 12/1988 |
| JP | 10-017523 | 1/1998 |
| WO | 99/13980 | 3/1999 |
| WO | 03/064035 | 8/2003 |

OTHER PUBLICATIONS

Carreon et al., 2009, Mesostructured mixed Mo-V-Mb oxides for propane ammoxidation, Catalysis communications, vol. 10, pp. 416-420.*

Cavani et al., 2007 Oxidative dehydrogenation of ethane and propane: How far from commercial implementation?, Catalysis today, vol. 127, pp. 113-131.*

Cavani, F. et al., Oxidative dehydrogenation of ethane and propane: How far from commercial implementation?, Catalysis Today, 127 (2007) 113-131.

Thorsteinson, E.M. et al., The oxidative dehydrogenation of ethane over catalysts containing mixed oxides of molybdenum and vanadium, Journal of Catalysis, 52 (1978) 116-132.

Ueda, W. et al., Selective oxidation of light alkanes over hydrothermally synthesized Mo-V-M-O (M=Al, Ga, Bi, Sb, and Te) oxide catalysts, Applied Catalysis A: General 200 (2000) 135-143.

Botella, P. et al., Selective oxidation of ethane: Developing an orthorhombic phase in Mo-V-X (X=Nb, Sb, Te) mixed oxides, Catalysis Today 142 (2009) 272-277.

Botella, P. et al., Selective oxidative dehydrogenation of ethane over MoVSbO mixed oxide catalysts, Applied Catalysis A: General 298 (2006) 16-23.

Ivars, F. et al., Selective propane oxidation over MoVSbO catalysts. On the preparation, characterization and catalytic behavior of M1 phase, Journal of Catalysis, 262 (2009) 35-43.

Al-Saeedi, J. et al., High-throughput experimentation in multicomponent bulk mixed metal oxides: Mo-V-Sb-Nb-O system for selective oxidation of propane to acrylic acid, Applied Catalysis A: General, 237 (2002) 111-120.

Ruth, K. et al., Mo-V-Nb oxide catalysts for the partial oxidation of Ethane. II Chemical and catalytic properties and structure function relationships, Journal of Catalysis, 175 (1998) 27-39.

Guerrero-Perez, M.O. et al., Niobium as promoting agent for selective oxidation reactions, Catalysis Today,142 (2009) 245-251.

English Abstract of Safonova, Olga V. et al., Mechanism of the Oxidation-Reduction of the MoVSbNbO Catalyst: In Operando X-Ray Absorption Spectroscopy and Electrical Conductivity Measurements. The Journal of Physical Chemistry B, 2006, vol. 110, No. 47, p. 23962-23967; Aparatados 1-2.

English Abstract of Novakova, Ekaterina K. et al., Propane Oxidation on Mo—V—Sb—Nb Mixed-Oxide Catalysts: 1. Kinetic and Mechanistic Studies. Journal of Catalysis, 2002, vol. 211, No. 1, p. 226-234; apartado Experimental and Methods.

International Preliminary Report on Patentability dated Apr. 21, 2015 and International Search Report dated Feb. 28, 2014 that issued in corresponding PCT Patent Application No. PCT/MX2013/000121.

* cited by examiner

Column A         Column B

OXIDATIVE DEHYDROGENATION OF ETHANE TO ETHYLENE AND PREPARATION OF MULTIMETALLIC MIXED OXIDE CATALYST FOR SUCH PROCESS

FIELD OF THE INVENTION

The present invention relates to the oxidative dehydrogenation of light paraffins using a tellurium-free multimetallic oxide catalyst. More particularly, it relates to preparation of highly active and selective catalysts for the oxidative dehydrogenation of ethane to produce ethylene at moderate temperatures, <500° C., without the formation of acetic acid and/or other oxygenated hydrocarbons.

The present invention provides catalysts based on mixed oxides, exhibiting an orthorhombic bronze-like structure, denominated as M1 crystalline phase, diffraction peaks appear at 2θ equal to 6.6±0.4, 7.7±0.4, 9.0±0.4, 22.2±0.4, 26.7±0.4, 26.8±0.4, 27.1±0.4; (ICSD 55097) and other crystalline structures that have an important role for obtaining high performance catalysts for the oxidative dehydrogenation of ethane to ethylene.

BACKGROUND OF THE INVENTION

Ethylene is the keystone of the petrochemical industry, since; it is employed as the main building block for the production of polymers, ethyl-benzene and styrene, among other chemical products of great importance in the modern world. Ethylene is produced from the steam-cracking (pyrolysis) of saturated hydrocarbon cuts, chiefly ethane and propane. Such processes are carried out in the presence of superheated steam at temperatures within the range 800-1000° C. Operating under these conditions involves a huge energetic demand and very high expenses related to the cost and maintenance of the furnaces which provide the heat required for the process. Also, due to the usage of high temperature, a wide variety of byproducts are formed, such as di-olefins as well as acetylene being the ones observed at the largest concentrations. The separation of these formed species from the reactor effluent requires a relatively complex scheme involving extractive distillation and/or selective hydrogenation, the latter in the particular case of having acetylene, which at the end requires of an additional investment. As a consequence, for economic and environmental reasons, several worldwide companies and research groups have focused their efforts on finding alternative process to produce ethylene.

An attractive route to produce ethylene is through the oxidative dehydrogenation reaction of ethane. The oxidative dehydrogenation of ethane (ODH-E) is an exothermic reaction which is not limited by the thermodynamic equilibrium and, hence, full ethane conversion is possible at low reaction temperatures (<500° C.). In the ODH-E, additionally, the number of side reactions is rather limited; usually, carbon monoxide and carbon dioxide appear as the main side products, while the formation of coke is negligible. Despite the many efforts dedicated to obtain catalysts with high activity and selectivity features, to the date, industrial application of ODH-E is still far from a reality. In fact, economic calculations have indicated that ethylene yields reported so far during ODH-E are not yet sufficient to be considered as an economically profitable process. It is therefore clear that more efforts are required to further improve the catalyst performance whilst, in the process context, particular attention is to be paid to design an adequate reactor configuration due to the thermal characteristics of the reactions involved.

Vanadium based catalysts supported on conventional materials were the first catalytic systems used for the ODH-E, notwithstanding, their efficiency to produce ethylene was not very high (Oxidative dehydrogenation of ethane and propane: commercial How far from implementation? Cavani et al., Catalysis Today, 127 (2007) 113). In particular, at high ethane conversions, an important amount of carbon oxides and acetic acid were observed in detriment to ethylene formation.

The use of catalysts based on oxides of molybdenum and vanadium together with other oxides of transition metals, e.g., Ti, Cr, Mn, Fe, Co, Ni, Nb, Ta or Ce, calcined at 400° C., was proposed by Thorsteinson et al. in "The Oxidative Dehydrogenation of Ethane over Catalyst Containing Mixed Oxides of Molybdenum and Vanadium", Journal of Catalysis, 52 (1978) 116. The best result was obtained over a solid with the composition $Mo_{0.61}V_{0.31}Nb_{0.08}$ supported in gamma alumina, yielding a 25% of ethylene at 340° C.

Later, in U.S. Pat. Nos. 4,250,346, 4,524,236 and 4,568,790 assigned to Union Carbide Corporation, the synthesis of catalyst for ODH-E at low temperature is reported. U.S. Pat. No. 4,524,236, in particular, discloses a catalyst with a composition MoVNbSbM (M being at least one of the following elements Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W). The best catalytic result offered in this patent was obtained over the $Mo_{0.61}V_{0.26}Nb_{0.07}Sb_{0.04}Ca_{0.02}$ system, exhibiting an ethane conversion equal to 34% and selectivity to ethylene of 86% when the reaction was conducted at 330° C. After a further increase in the reaction temperature to 400° C., 73% of the fed ethane was converted with an ethylene selectivity of 71%. In reference U.S. Pat. No. 4,250,346, the formation of acetic acid is reported to occur during the ODH-E.

In U.S. Pat. No. 5,162,578, granted to Union Carbide Chemicals & Plastics and Union Carbide Corporation, and EP 0294846A3 with Union Carbide Corporation as applicant, McCain and co-workers claim about a catalytic composition with a general formula $Mo_aV_vNbSbX_e$ (X being at least one of the following metals Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W, preferably Ca) to produce acetic acid from ethane, or a mixture ethane/ethylene, with a remarkably high selectivity to the mentioned acid.

Japanese patent JP 10143314 granted to Mitsubishi Chemical Industries Ltd. describes a MoVSbX catalytic system (wherein X corresponds to Ti, Zr, Nb, Ta, Cr, W, Mn, Fe, Ru, Co, Rh, Ir, Ni, Pd, Pt, Cu, Ag, Zn, In, Sn, Pb, Bi, Ce and alkaline rare earth metals) which exhibits a crystalline structure defined by a X-ray spectrum included in the patent. The catalytic system was used for the selective oxidation of ethane to ethylene with ethane conversions as high as 90.8% and selectivity to ethylene of 68%.

MoVNbSb mixed oxides have been also proposed as effective catalysts for the oxidative dehydrogenation of ethane to produce ethylene, as well as acetic acid, in patent EP-A-0294845 granted to Union Carbide.

WO 99/13980, assigned to Saudi Basic Ind., in turn, reports a Mo—V-Nb based catalyst doped with small amounts of P, Hf, Te and/or As. Solids were thermally treated under air atmosphere between 250 and 450° C. and then used in the oxidation of ethane to produce acetic acid, reporting yields within the 12-17% range.

In Japanese Patent JP10017523 granted to Mitsubishi Chemical Industries Ltd. in 1998, inventors proposed a catalyst for the oxidation of ethane to acetic acid. It is composed of a metal—Ru, Rh, Jr Pd and/or Pt—supported over a mixed oxide of MoVXZ. In this patent, particular attention is paid on a Pd based catalyst supported on a mixed oxide constituted of MoVNbSb, which exhibited yields to acetic acid as high as 59.7%.

Several US patents, in particular U.S. Pat. Nos. 6,030,920A, 6,194,610B1, 6,310,241B1, 6,383,977B1 and U.S. 2003/0100794A1 have been granted to Saudi Basic Industries Corporation, a Saudi Arabian company. These patents report on the performance of Mo and V based catalysts promoted with other metals for the oxidative dehydrogenation of ethane at low temperatures. The catalytic activity experiments contained in these documents, however, were carried out using molecular oxygen as an oxidant to yield mainly acetic acid, while ethylene is formed as byproduct.

In U.S. 2003/01000794A1, a new catalyst with a general formula $MO_aV_bAl_cX_dY_eO_z$, where in X is at least one of the elements belonging to the group W and Mn; Y is at least one element selected from the group Pd, Sb, Ca, P, Ga, Ge, Si, Mg, Nb and K; an "z" is an integer number representing the number of oxygen atoms required to satisfy the valence of Mo, V, Al, X and Y. These catalysts were utilized in the partial oxidation of ethane to produce acetic acid as well as ethylene.

Additionally, methods to produce catalyst containing Mo, V, Sb and Nb are also claimed in U.S. Pat. Nos. 6,610,629 B2 and 7,109,144 B2, both assigned to Asahi Kasei Kabushiki Kaisha. The composition of the catalyst is represented by the general formula $Mo_{1.0}V_aSb_bNb_cZ_dO_n$. In the latter, Z corresponds to at least an element belonging to the group W, Cr, Ti, Al, Ta, Zr, Hf, Mn, Fe, Ru, Co, Rh, Ni, Pd, Pt, Zn, B, In, Ge, Sn, Pb, Bi, Y, Ga, rare earths and alkaline rare earth metals. These catalysts were employed in the ammoxidation of propane or isobutene.

In U.S. 2008/0161602A1, which claims the benefits from the provisional application patent U.S. Ser. No. 60/877,270, describes a catalytic formulation denoted by the general formula $Mo_aV_bNb_cTe_dSb_eO_f$, wherein a=1, b=0.01-1.0, c=0.1-1.0, d=0.1-1.0 e=0.01-1.0 and f depend upon the oxidation state of the other elements. A particular feature of these catalysts is to exhibit at least two crystalline phases, namely, an orthorhombic one denoted as M1 and a second pseudo-hexagonal phase named M2. The referred solid is used to promote the partial oxidation of propane to acrylic acid, acetic acid being one of the most important side-product.

U.S. 2011/0245571A1 and U.S. 2012/0016171A1, to Nova Chemicals International S.A., claim a process for the preparation of a catalyst for the oxidative dehydrogenation of ethane, with a relatively high yield to ethylene reporting selectivity to ethylene higher than 90% with productivity in the range 2,500 g ethylene per hour and kg of catalyst. The catalyst claimed is a tellurium-containing solid with as general formula $V_xMo_yNb_zTe_mMe_nO_p$, wherein Me is a metal belonging to the group Ta, Ti, W, Hf, Zr and Sb, or a mixture of them. Metals are deposited over a matrix composed of oxides of Ti, Zr, Al, Mg, La, Si or mixtures thereof, or even a matrix of carbon.

U.S. 2010/0256432A1, assigned to Lummus Novolent GMBH/Lummus Technology Inc., and U.S. Pat. No. 8,105,971 B2 to Lummus Technology Inc., claim a high performance catalyst for the oxidative dehydrogenation of ethane to ethylene. Over this catalytic system represented by $Mo_{1.0}V_{0.29}Nb_{0.17}Sb_{0.01}Te_{0.125}O_x$, ethane conversion reached values of up to 81% with an ethylene selectivity of 89% when reaction is conducted at 360° C. Notice that this solid also contains tellurium as an ingredient of the formulation.

U.S. 2006/0183941A1, J. L. Dubois, W. Ueda et al., in contrast, claims a tellurium-free catalyst represented by the general formula $Mo_{1.0}V_aSb_bNb_cSi_dO_x$, in which a=0.006-1.0, b=0.006-1.0, c=0.006-1.0, d=0-3.5 and "x" is the amount of oxygen bonded to other elements. The catalyst is applied to the partial oxidation of propane to yield acrylic acid.

One of the most efficient catalysts for the oxidative dehydrogenation of ethane to ethylene has been described in WO 03/064035 and U.S. Pat. No. 7,319,179, by J. M. Lopez-Nieto et al., and granted to UPV-CSIC. There is claimed a catalyst based on a mixture of mixed oxides, MoTeVNb, which exhibited a yield to ethylene close to 75%. This high-efficiency solid contains tellurium as well.

Similar catalysts have been reported in the open literature. Ueda et al. in "Selective oxidation of light alkanes over hydrothermally synthesized Mo—V-M-O (M=Al, Ga, Bi, Sb, and Te) oxide catalysts", Applied Catalysis A: General 200 (2000) 135. The formation of acetic acid is, however, always observed in the reactor effluent. Selectivity to ethylene is lower than 75% for an ethane conversion lower than 20%.

Also, Botella et al. in "Selective oxidation of ethane: Developing an orthorhombic phase in Mo—V—X(X=Nb, Sb, Te) mixed oxides", Catalysis Today 142 (2009) 272, used a MoVSb based catalyst for the ODH-E with a capacity to convert ca. 40% ethane and a selectivity to ethylene in the 90-92% range.

Due to the economic, technical and environmental advantages that the process for producing ethylene by the oxidative dehydrogenation of ethane has exhibited, the attention of research groups has been focused mainly on improving the catalyst formulation. One of the main challenges to be solved is the minimization of the formation of byproducts, in particular carbon oxides ($CO_x$). These compounds, apart from decreasing the global efficiency of the process, are produced via very exothermal reactions. Thus, catalysts with a high potential to be used at the industrial scale are expected to display selectivity to ethylene between 80 and 85% for ethane conversion in the range 50-60%. Moreover, the formation of oxygenate products, e.g., acetic acid and aldehydes, must be avoided on the referred catalytic systems as their presence would involve additional stages in the separation train or troubles in the reactor.

On the other hand, the presence of tellurium seems to be indispensable in most of the high efficiency catalytic systems reported in many patents to date for the oxidative dehydrogenation of ethane to ethylene. Notwithstanding, the relatively high susceptibility of tellurium to reducing atmospheres, together with the large amount of metal that is lost during the thermal activation stages, appears to be a restriction for a catalyst scaling-up to industrial level. This problem would be always latent in industrial practice since, during operation, the reaction mixture can be composed of ethane diluted in nitrogen, i.e., a reductive mixture which, in the presence of hot-spots would favor the reduction and further loss of tellurium with the consequent gradual decay in the catalytic properties of the solid.

SUMMARY OF THE INVENTION

A highly selective process for the oxidative dehydrogenation of ethane to ethylene has been discovered, which process comprises contacting ethane and an oxidizing agent under oxidative dehydrogenation reaction conditions with a tellurium-free, multimetallic mixed oxide solid catalyst having the formula $$MoV_hSb_iA_jO_x \qquad (I)$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, $0 \le j \le 2.0$, the ratio i/h is between 0.3 and 10.0, and x represents the number determined by and consistent with the valence requirements of the other elements present in the multimetallic mixed oxide. The resulting catalyst has an M1 crystalline phase, and one or more additional crystalline phases, which result in a highly active and selective oxidative dehydrogenation catalyst for the conversion of ethane to ethylene without the presence of tellurium in the catalyst composition.

The catalyst of formula I can be prepared by either:

A) a process which comprises forming a tellurium-free mixture of molybdenum, vanadium and antimony metallic precursors and a structure-directing compound selected from the group consisting of primary amines, secondary amines, tertiary amines, ammonia, tetra-methyl ammonium and hydrazine, and subjecting said tellurium-free mixture to hydrothermal conditions to form a solid, washing and drying said solid, and thermally activating said dried solid to form a catalyst having one or more crystalline phases in addition to the M1 crystalline phase; or B) a process which comprises forming a tellurium-free mixture of molybdenum, vanadium and antimony metallic precursors and thermally treating said tellurium-free mixture of mixture to form an MoVSb solid, doping said MoVSb solid with a doping metal cation represented by said A, and thermally activating the A metal cation-doped MoVSb solid to form a catalyst having one or more crystalline phases in addition to the M1 crystalline phase.

Remarkably, it has been found that by preparing the catalyst of Formula I by either such process, the oxidative dehydrogenation of ethylene using the resulting catalyst provides catalytic performance superior to the MoVSb obtained by a typical hydrothermal method despite the absence of tellurium in the present catalyst.

According to one embodiment of the invention, the multimetallic mixed oxide solid catalyst of Formula I is prepared by a process which comprises forming a tellurium-free mixture of molybdenum, vanadium and antimony metallic precursors and a structure-directing compound selected from the group consisting of primary amines, secondary amines, tertiary amines, ammonia, tetra-methyl ammonium and hydrazine, and subjecting said tellurium-free mixture to hydrothermal treatment to form a solid, washing and drying said solid, and activating said dried solid to form a catalyst having one or more crystalline phases in addition to the M1 crystalline phase. Preferred structure-directing compounds are methylamine, dimethyl amine, tri-methyl amine, diethyl amine, or mixtures thereof. The hydrothermal treatment may be conducted at a temperature between 100-200° C. for 6-150 hours and the resulting solids are washed and dried at 80-120° C., prior to activation. Preferred hydrothermal treatment is conducted at a temperature between 150-180° C. for 12-48 hours.

Activation of the dried solids involves a first thermal treatment at a temperature in the range of from about 150 to about 350° C. under oxidizing and/or reducing and/or inert atmosphere for 1 to 5 hours; and then a second thermal treatment at a temperature in the range of from about 150 to about 700° C. under an oxidant or inert atmosphere for 1 to 5 hours.

According to another embodiment of the invention the multimetallic mixed oxide solid catalyst is prepared by a process which comprises forming a tellurium-free mixture of molybdenum, vanadium and antimony metallic precursors and thermally treating said tellurium-free mixture to form an MoVSb solid, doping said MoVSb solid with a doping metal cation selected from the group consisting of Nb, Cu, W, Bi, Sn, Ti, Fe, Co, Ni, Cr, Ga, Zr, rare earth elements, alkali metal or alkaline earth metal, as salts, oxides, hydroxides, or alkoxides, and thermally activating the metal cation-doped MoVSb solid to form a catalyst having one or more crystalline phases in addition to the M1 crystalline phase. Preferably, the doping metal cation is Nb, W, Sn, Cu or K. According to this embodiment, the MoVSb solid is heated to a temperature in the range of from about 150 to about 700° C. prior to doping said MoVSb solid and then activating the metal cation-doped MoVSb solid at a temperature in the range of from about 150 to about 700° C. under an oxidizing or inert atmosphere for about 1 to 5 hours.

According to further embodiment of the present invention, a multimetallic mixed oxide having the formula

$$MoV_hSb_iO_x \quad (II)$$

wherein h and i, respectively, are each between 0.001 and 4.0, the ratio i/h is between 0.3 and 10.0, and x represents the number determined by and consistent with the valence requirements of the other elements present in the multimetallic mixed oxide, is prepared by a process, which comprises, forming a tellurium-free mixture of molybdenum, vanadium and antimony metallic precursors and a structure-directing compound selected from the group consisting of primary amines, secondary amines, tertiary amines, ammonia, tetra-methyl ammonium and hydrazine, and subjecting said tellurium-free mixture to hydrothermal conditions to form a solid, washing and drying said solid, and thermally activating said dried solid to form a catalyst having one or more crystalline phases in addition to the M1 crystalline phase. The preferred structure-directing compound is methylamine, dimethyl amine, tri-methyl amine, diethyl amine, or mixtures thereof. The hydrothermal treatment is conducted at a temperature between 100-200° C. for 6-150 hours and the resulting solids are washed and dried at 80-120° C. prior to activation. Preferably, the hydrothermal treatment is at a temperature between 150-180° C. for 12-48 hours. Activation involves a first thermal treatment at a temperature in the range of from about 150 to about 350° C. under oxidant and/or reducing and/or inert atmosphere for 1 to 5 hours; and a second thermal treatment at temperatures ranging from about 150 to about 700° C. under an oxidant or inert atmosphere for 1 to 5 hours.

According to a preferred embodiment of the invention, the multimetallic mixed oxide having the formula

$$MoV_hSb_iO_x \quad (II)$$

wherein h and i, respectively, are each between 0.001 and 4.0, the ratio i/h is between 0.3 and 10.0, and x represents the number determined by and consistent with the valence requirements of the other elements present in the multimetallic mixed oxide, is prepared by a process, which comprises, forming a tellurium-free aqueous solution of metallic precursors consisting of molybdenum, vanadium and antimony and a structure-directing compound selected from the group consisting of primary amines, secondary amines, tertiary amines, ammonia, tetra-methyl ammonium and hydrazine, and subjecting said tellurium-free mixture to hydrothermal conditions to form a solid, washing and drying said solid, and thermally activating said dried solid to form a catalyst having one or more crystalline phases in addition to the M1 crystalline phase. The preferred structure-directing compound is methylamine, dimethyl amine, tri-methyl amine, diethyl amine, or mixtures thereof. The hydrothermal treatment and activation are conducted as previously described. In this embodiment the only metallic precursors in admixture with the structure-directing compound are molybdenum, vanadium and antimony. Thus, other metals or metal-precursors, such as niobium, are excluded from the solution or mixture, and the base metals of the catalyst are only molybdenum, vanadium and antimony.

Another embodiment involves formation of a multimetallic mixed oxide having the formula $$MoV_hSb_iA_jO_x \quad \text{(III)}$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, $0.0001 \leq j \leq 2.0$, the ratio i/h is between 0.3 and 10.0, and x represents the number determined by and consistent with the valence requirements of the other elements present in the multimetallic mixed oxide, said catalyst having an M1 crystalline phase, and one or more additional crystalline phases, said process comprising, forming a tellurium-free mixture of molybdenum, vanadium and antimony metallic precursors and thermally treating said tellurium-free mixture of mixture to form an MoVSb solid, doping said MoVSb solid with a doping metal cation represented by said A, and thermally activating the A metal cation-doped MoVSb solid to form a catalyst having one or more crystalline phases in addition to the M1 crystalline phase. The preferred doping metal cation is Nb, W, Sn, Cu or K. The MoVSb solid is heated a temperature in the range of from about 150 to about 700° C. prior to doping said MoVSb solid and then activating said metal cation-doped MoVSb solid at a temperature in the range of from about 150 to about 700° C. under an oxidizing or inert atmosphere for about 1 to 5 hours.

According to a preferred embodiment of the invention the multimetallic mixed oxide having the formula $$MoV_hSb_iA_jO_x$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, $0.0001 \leq j \leq 2.0$, the ratio i/h is between 0.3 and 10.0, and x represents the number determined by and consistent with the valence requirements of the other elements present in the multimetallic mixed oxide, is prepared by a process comprising the steps,
(a) forming a tellurium-free mixture of metallic cations, which metallic cations preferably consist of molybdenum, vanadium and antimony cations,
(b) thermally treating the tellurium-free mixture to form an MoVSb solid,
(c) calcining the tellurium-free MoVSb solid at a temperature in the range of from about 150 to about 700° C., in an inert atmosphere, for about 1 to about 5 hours;
(d) doping the MoVSb solid by adding a metal cation represented by A, such as Nb, W, Sn, Cu or K, and
(e) calcining the A metal cation-doped MoVSb solid 150 to about 700° C., in an inert atmosphere, preferably under nitrogen, for about 1 to about 5 hours to form a catalyst having one or more crystalline phases in addition to the M1 crystalline phase.

Each of the steps (a) through (e) are conducted in the absence of added oxygen and added $H_2O_2$. The expression "absence of added oxygen" means no air or gas containing oxygen is introduced in any process step through the second calcining step Likewise, the expression "absence of added $H_2O_2$", means that no $H_2O_2$ is introduced in any process step. In this preferred embodiment of the invention, no metal cation other than a Mo, V or Sb cation is present during formation of the catalyst until the A metal cation, such as Nb, is added.

Thus, the present invention relates to preparation methods for obtaining tellurium-free multimetallic mixed oxide catalysts, their activation process and their use in the partial oxidation of ethane to ethylene.

Remarkably, use of the tellurium-free multimetallic mixed oxide catalysts of the present invention for the oxidative dehydrogenation of ethane, result in high conversion of ethane and high selectivity to ethylene, at moderate temperatures (<500° C.), without formation of oxygenated hydrocarbons, as demonstrated in FIG. 18, which corresponds to the catalysts prepared in accordance with example 21.

Figure 11:
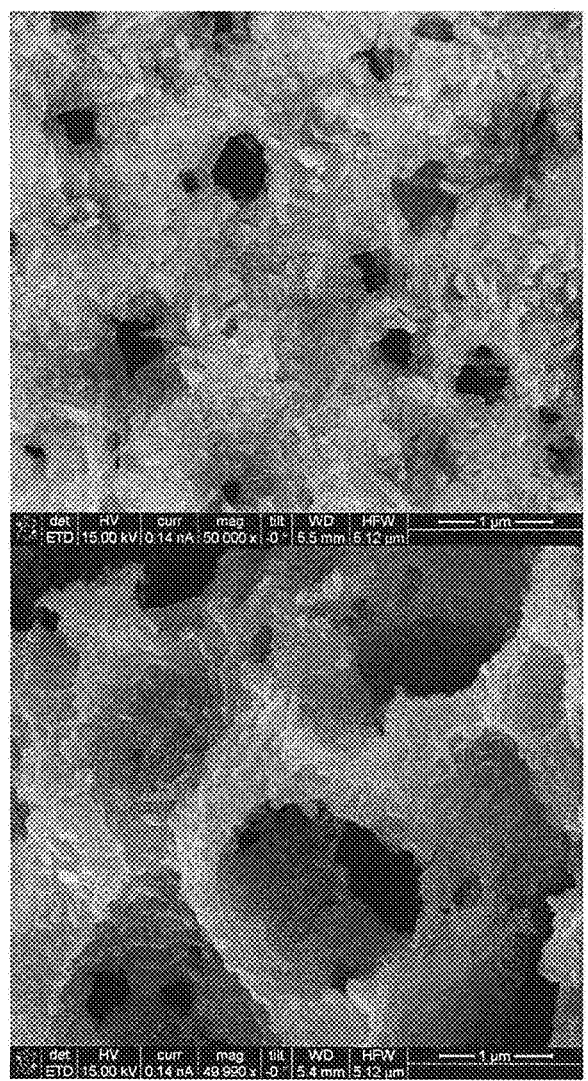
Figure 12:
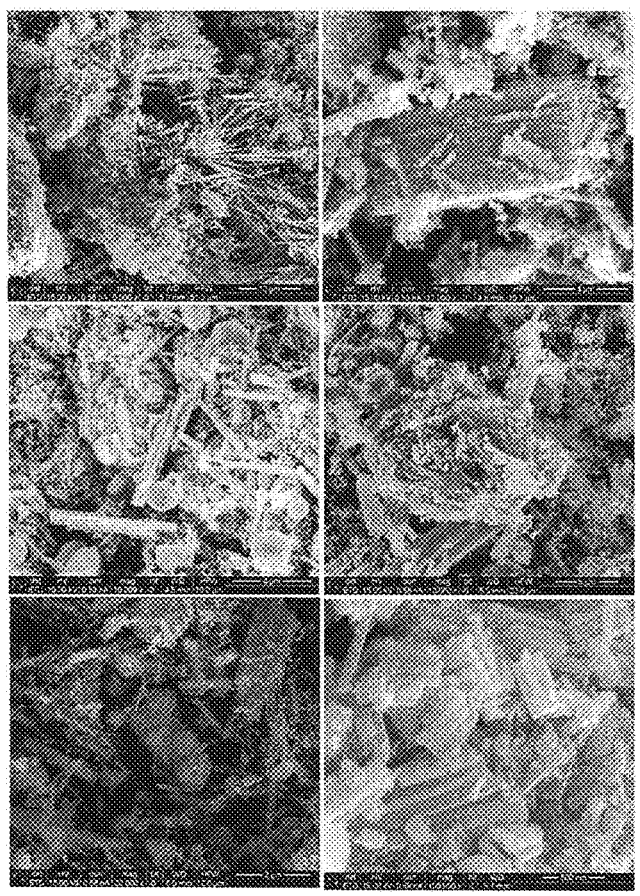
Figure 13:
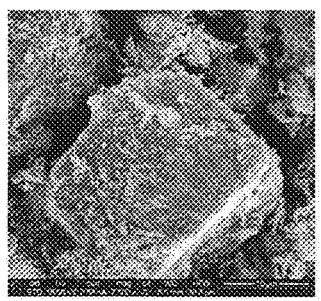
Figure 13:
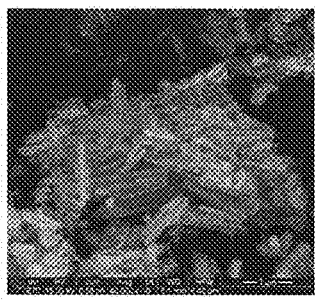
Figure 13:
Figure 13:
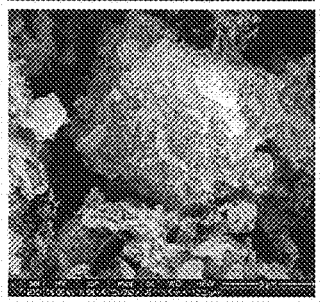
Figure 13:
Figure 13:
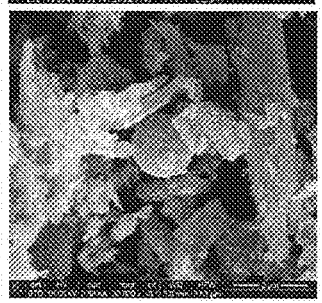
Figure 14:
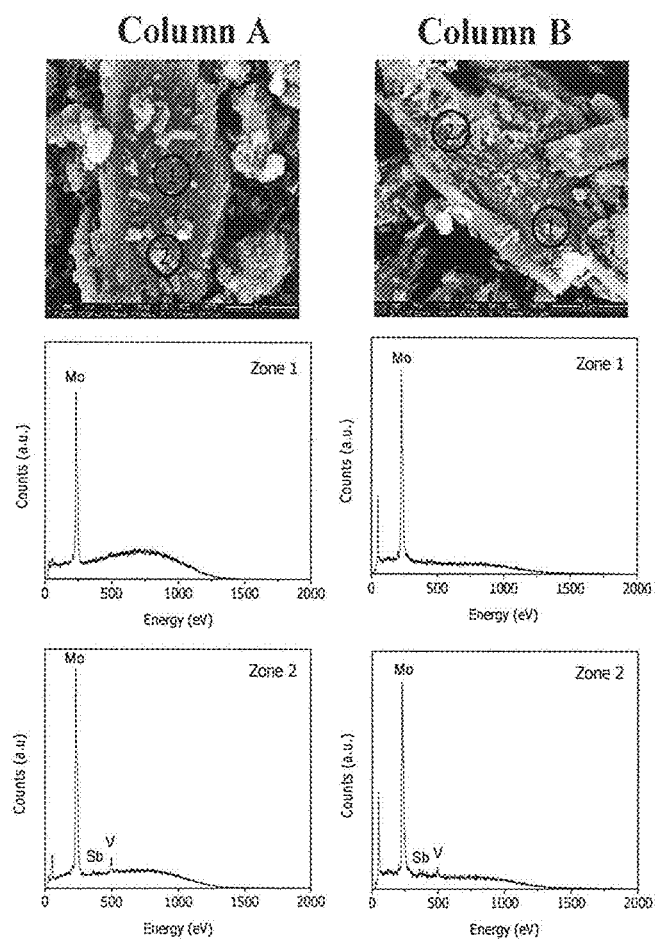
Figure 15:
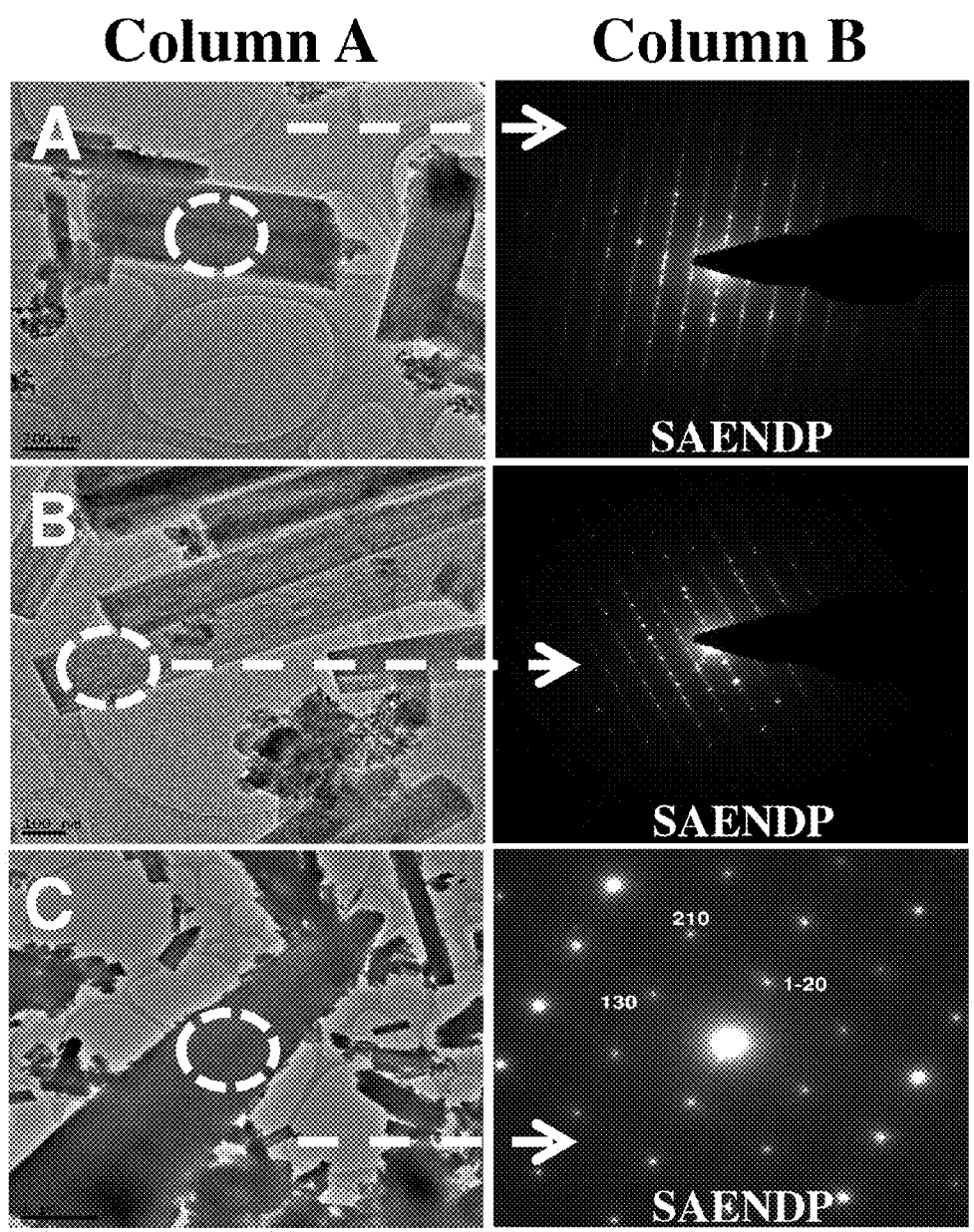
Figure 16:
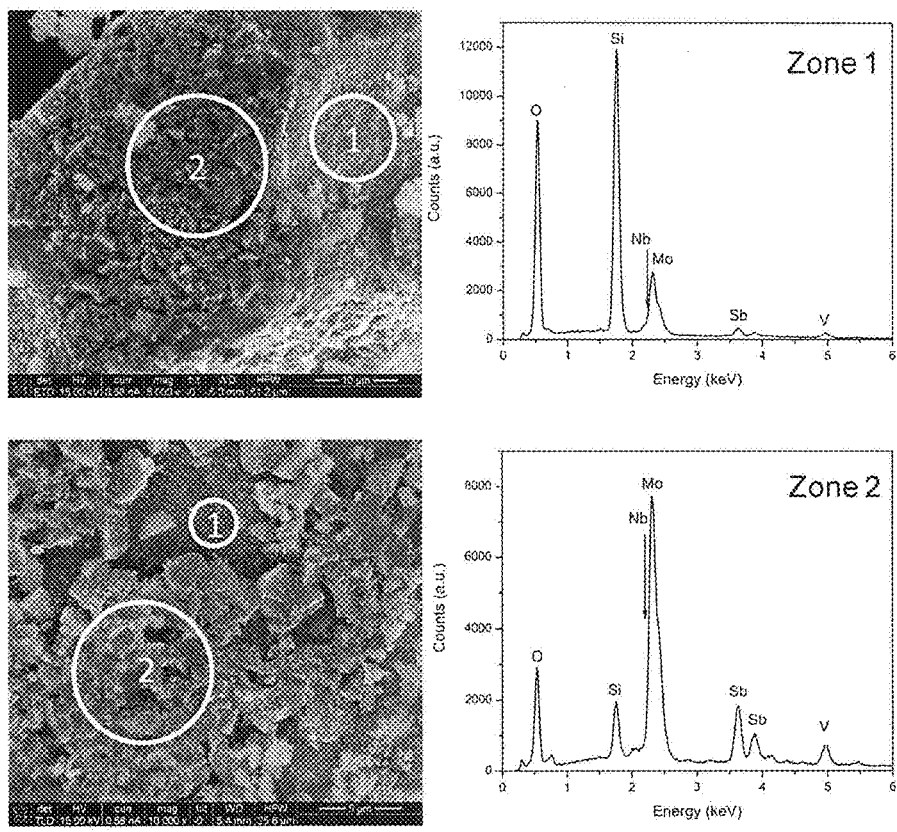
Figure 17:
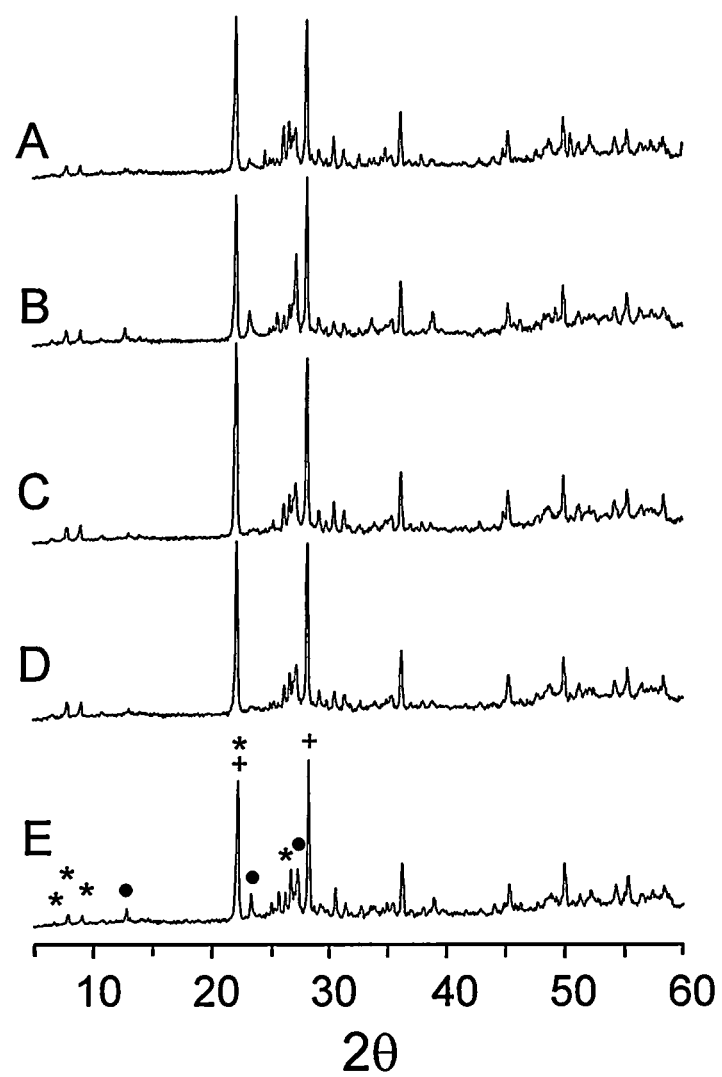
Figure 18:
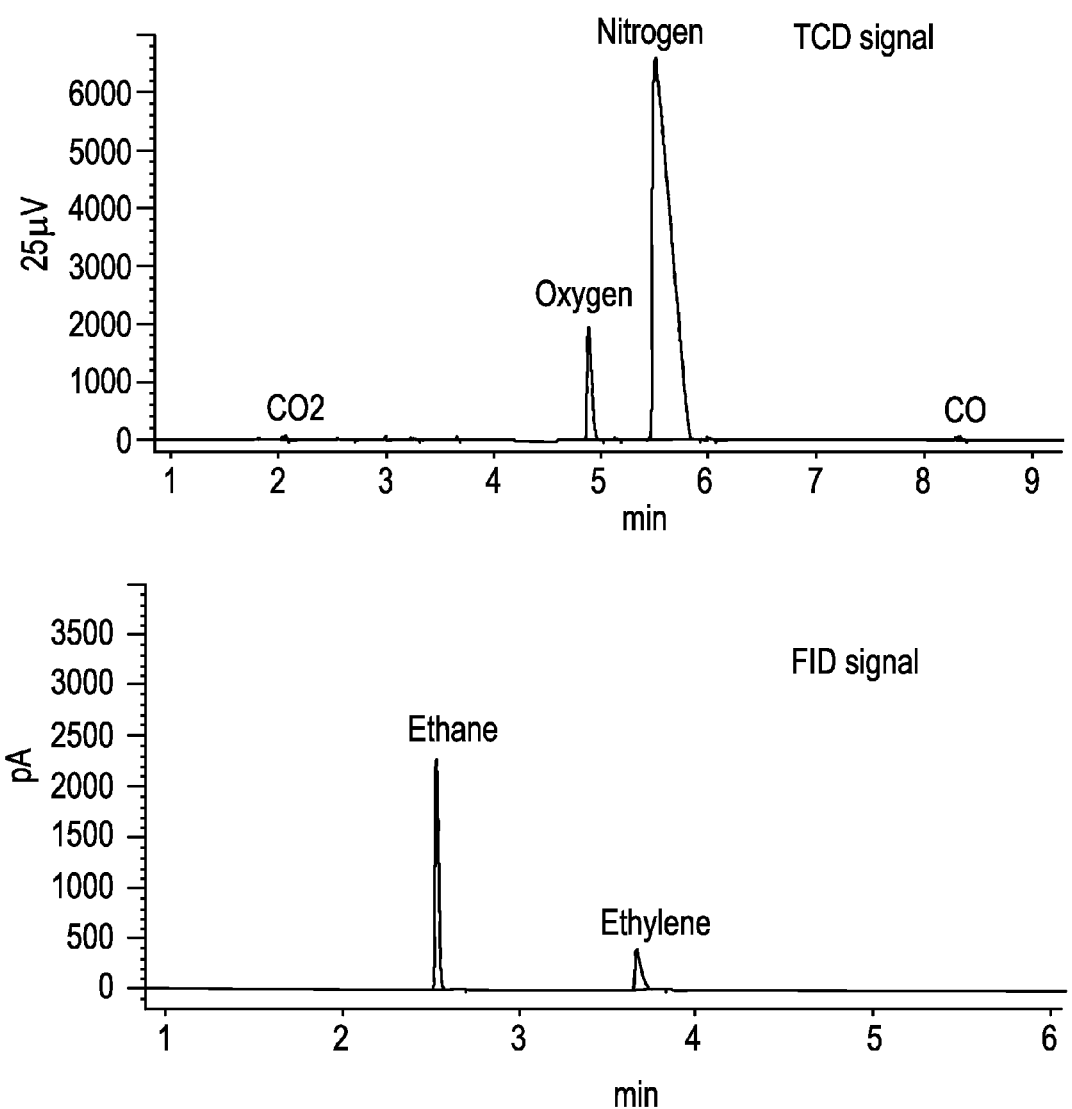

under air atmosphere followed by a second thermal treatment at 600° C. under nitrogen flow. Symbol [*] denotes phase M1, and [+] phase M2, and [●] MoO₃;

FIG. 11 are Scanning Electron Microscopy images of the catalyst prepared according to Example 8, after drying at 100° C. This morphology is representative of solids prepared by the hydrothermal method here described;

FIG. 12 are Scanning Electron Microscopy images of the catalyst prepared according to Example 23. (Column A) Images of the solid dried at 100° C., and (Column B) images of the catalyst subjected to a thermal treatment at 250° C. under air atmosphere followed by a second thermal treatment at 600° C. under nitrogen flow;

FIG. 13 are Scanning Electron Microscopy images of a catalyst prepared according to Example 28. (Column A) Images of the solid dried at 100° C. and (Column B) images of the catalyst subjected to a thermal treatment at 250° C. under air atmosphere followed by a second thermal treatment at 600° C. under nitrogen flow;

FIG. 14 are Scanning Electron Microscopy images, with elemental chemical analysis within the selected zones (bottom part), by Electron Dispersive Spectroscopy technique. (Column A) catalyst of Example 23 and (Column B) catalyst of Example 28. Both catalysts included in this figure were subjected to thermal treatment at 250° C. under air atmosphere followed by a second thermal treatment at 600° C. under nitrogen flow;

FIG. 15 are (Column A) High Resolution of Transmission Electronic Microscopy images and of the crystals present in the catalyst prepared in accordance to Example 23. (Column B) are Selected Area Electron Nano-Diffraction Patterns (SAENDP) corresponding to the white encircled area marked over a selected crystal of the column A. These images, are in agreement with the XRD patterns shown in the FIG. 7, thus, confirming the presence of the several crystalline phases. (A) Image corresponds to a crystal of M1 phase, which confirmed by its electrons nano-diffraction pattern (right side), (B) Image corresponds to a crystal of M2 phase, which confirmed by its electrons nano-diffraction pattern (right side), and (C) Image corresponds to a crystal of MoO₃ phase, which confirmed by its electrons nano-diffraction pattern (right side). Such catalyst has been treated thermally at 250° C. under air atmosphere followed by a second thermal treatment at 600° C. under nitrogen flow;

FIG. 16 are Scanning Electron Microscopy images with elemental chemical analysis (right side) within the selected zones by Electron Dispersive Spectroscopy technique of the catalyst prepared in accordance with Example 29. The catalyst was subjected to thermal treatment at 600° C. under nitrogen flow;

FIG. 17 are XRD spectra of catalysts prepared in accordance with: (A) Example 10, (B) Example 11, (C) Example 12, (D) Example 13 and (E) Example 14. Symbol [*] denotes phase M1, [+] phase M2, and [●] MoO₃; and FIG. 18 are chromatographic signals obtained during catalytic testing of catalysts prepared in accordance with example 21, indicating absence of oxygenated hydrocarbons during oxidative dehydrogenation of ethane to ethylene.

DETAILED DESCRIPTION OF THE INVENTION

Catalysts of the present invention may be represented by the general formula MoVSbA, wherein A is one of the following elements: Nb, W, Ga, Bi, Sn, Ti, Fe, Co, Cu, Ni, Cr, Zr, rare earth metals, alkaline metals or alkaline rate earth metals or a mixture of thereof. According to another embodiment, the catalyst may be represented by the formula MoVSb.

The present invention involves the oxidative dehydrogenation of light paraffins to produce olefins, more specifically, a procedure to perform the oxidative dehydrogenation of ethane to ethylene by means of a process wherein ethane is contacted with oxygen or with an oxygen containing stream, and/or with another oxidant agent, over a catalyst composed of mixed multimetallic oxides. The catalyst is a tellurium-free solid, containing Mo, V and Sb, and may include optionally an A metal, the latter one selected from the following list: Nb, W, Ga, Bi, Sn, Cu, Ti, Fe, Co, Cu, Ni, Cr, Zr, rare earth metals or rare earth alkaline metals or mixtures of thereof. The catalyst, in the thermally-treated form, is represented by the general formula MoVSbAO corresponding to a solid in which metallic elements are in combination with oxygen to produce a mixture of metallic oxides, with variable oxidation states.

In a preferred embodiment of the invention, molybdenum, vanadium and antimony are present in the form of a thermally-treated mixed oxide in the catalyst formulation having the formula,

$$MoV_hSb_iO_x \qquad (II)$$

wherein h and i, respectively, are each between 0.001 and 4.0, the ratio i/h is between 0.3 and 10.0, and x represents the number determined by and consistent with the valence requirements of the other elements present in the multimetallic mixed oxide.

In this embodiment, the catalyst is prepared by a process, which comprises, forming a tellurium-free mixture of molybdenum, vanadium and antimony metallic precursors in solution with a "structure-directing" compound selected from the group consisting of primary amines, secondary amines, tertiary amines, ammonia, tetra-methyl ammonium and hydrazine, and subjecting said tellurium-free mixture to hydrothermal conditions to form a solid. The resulting solid is washed and dried, and thereafter thermally activating to form a catalyst having one or more crystalline phases in addition to the M1 crystalline phase, such as the M2 and/or MoO₃ crystalline phases. It is especially preferred that the only metals in the catalyst in admixture with the structure-directing compound are the MoVSb base metals without any additional or promoter metal Likewise, after activation and formation of the M1 crystalline phase, no further or post treatment is required to provide a highly active and selective catalyst.

The preferred structure-directing compound is methylamine, dimethyl amine, tri-methyl amine, diethyl amine, or mixtures thereof. The hydrothermal treatment is conducted at a temperature between 100-200° C. for 6-150 hours and the resulting solids are washed and dried at 80-120° C. prior to activation. Preferably, the hydrothermal treatment is at a temperature between 150-180° C. for 12-48 hours. Activation involves a first thermal treatment at a temperature in the range of from about 150 to about 350° C., preferably 160 to about 300° C., under oxidant and/or reducing and/or inert atmosphere for 1 to 5 hours; and a second thermal treatment at temperatures ranging from about 150 to about 700° C., preferably, 550 to 650 under an oxidant or inert atmosphere for 1 to 5 hours.

In another preferred embodiment, the catalyst has the empirical formula:

$$MoV_hSb_iA_jO_x \qquad (III)$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, 0.0001≤j≤2.0, the ratio i/h is between 0.3 and 10.0, and x represents the number determined by and consistent with the valence requirements of the other elements present in the multimetallic mixed oxide, said catalyst having an M1 crystalline phase, and one or more additional crystalline phases, said process comprising, forming a tellurium-free mixture of molybdenum, vanadium and antimony metallic precursors and thermally treating said tellurium-free mixture of mixture to form an MoVSb solid, doping said MoVSb solid with a doping metal cation represented by said A, and thermally activating the A metal cation-doped MoVSb solid to form a catalyst having one or more crystalline phases in addition to the M1 crystalline phase. The preferred doping metal cation is Nb, W, Sn, Cu or K. The MoVSb solid is heated a temperature in the range of from about 150 to about 700° C. prior to doping said MoVSb solid and then activating said metal cation-doped MoVSb solid at a temperature in the range of from about 150 to about 700° C. under an oxidizing or inert atmosphere for about 1 to 5 hours. Since "x" depends on the oxidation state of Mo, V, Sb and A elements, the amount of oxygen in the catalyst represented by "x" does not only depends on the chemical composition, but mainly on the activation process employed, since the proper combination of oxidant and/or reducing agents allows to tune the oxidation state of the metallic atoms, so generating highly active and selective catalysts.

An especially preferred embodiment of the invention involves formation of a multimetallic mixed oxide having the formula

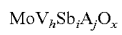

$$MoV_hSb_iA_jO_x$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, $0.0001 \leq j \leq 2.0$, the ratio i/h is between 0.3 and 10.0, and x represents the number determined by and consistent with the valence requirements of the other elements present in the multimetallic mixed oxide, said catalyst having an M1 crystalline phase, and one or more additional crystalline phases, said process comprising the steps, (a) forming a tellurium-free mixture of metallic cations, said metallic cations consisting of molybdenum, vanadium and antimony cations, (b) thermally treating the tellurium-free mixture to form an MoVSb solid, (c) calcining the tellurium-free MoVSb solid at a temperature in the range of from about 150 to about 700° C., in an inert atmosphere, for about 1 to about 5 hours;

(d) doping the MoVSb solid by adding a metal cation represented by A, such as Nb, W, Sn, Cu or K, and (e) calcining the A metal cation-doped MoVSb solid 150 to about 600° C., in an inert atmosphere, preferably under nitrogen, for about 1 to about 5 hours to form a catalyst having one or more crystalline phases in addition to the M1 crystalline phase, Each of the steps (a) through (e) are conducted in the absence of added oxygen and added $H_2O_2$. The expression "absence of added oxygen" means no air or gas containing oxygen is introduced in any process step through the second calcining step Likewise, the expression "absence of added $H_2O_2$", means that no $H_2O_2$ is introduced in any process step. In this preferred embodiment of the invention, no metal cation other than a Mo, V or Sb cation is present during formation of the catalyst until the A metal cation, such as Nb, is added.

In an additional preferred embodiment, A correspond to Nb, W, Ga, Bi, Sn, Ti, Fe, Co, Cu, Ni, Cr, Zr, rare earth metals, alkaline metals, or alkaline rare earth metals, or mixtures thereof.

In another preferred embodiment, A represents Nb, W, Sn, Cu, K or mixtures thereof.

In a preferred embodiment, the as-prepared multimetallic mixed oxides and/or the activated ones, thermally-treated, containing Mo, V and Sb in the form of at least one mixed oxide in the catalyst formulation.

After thermal treatment performed to activate solids, the thermally treated solid exhibits an X-ray pattern with several diffraction lines. The most important diffraction lines present in the activated solid must be located at 2θ equal to 6.6±0.4, 7.7±0.4, 9.0±0.4, 22.2±0.4, 26.7±0.4, 26.8±0.4, 27.1±0.4; which corresponds to the orthorhombic bronze-like structure, denominated as M1 crystalline phase (ICSD 55097). This phase has been recurrently claimed as the most active for oxidative dehydrogenation of ethane to ethylene. Thus, many efforts have been driven to produce solids with sole M1 phase. However, the activated solids prepared according to the methods presented in this invention, often show XRD patterns with additional diffraction lines, denoting the presence of other metallic oxides, which are also part of the composition of the multimetallic catalytic system. It is worth noticing that those activated solids are remarkably more active and selective in the oxidative dehydrogenation of ethane to ethylene, even compared with those exhibiting the sole M1 phase. As seen in the XRD patterns shown in FIGS. 2 to 7, 9, 10 and 17, and microscopy images reported in FIGS. 14 to 16, where the presence of crystalline structures in addition to the M1 phase are detected. The resultant solid is highly active and selective catalysts for the oxidative dehydrogenation of ethane to ethylene.

The catalyst may be supported over a solid, such as, silica, silica gel, amorphous silica, zirconium oxide, silicon carbide, alumina, titanium oxide, cordierite, kaolin, aluminum-silicates or a mixture thereof, the FIG. 16 is presented as illustration. The amount of the selected support ranges from 20 to 70 wt. % of the total catalyst weight. Likewise, the catalyst can be a multimetallic mixed oxide in self-supported form, and/or in strong interaction with the crystalline phase obtained and/or segregated from the metallic elements initially present in the solid precursor, as it is confirmed in FIGS. 10C and 14. In this respect, the segregated metallic oxide allows the formation of crystals of a nanometric size of the M1 active phase of the multimetallic mixed oxide, increasing in this way the number of active sites in the catalyst. In a preferred form, it is desirable that the segregated phase be the crystalline phase of the molybdenum oxide ($MoO_3$) and/or M2 phase, which facilitate the dispersion of nanometric crystals of the multimetallic mixed oxide, mostly M1 phase.

Preparation Methods of Multimetallic Mixed Oxides

The multimetallic mixed oxides catalyst can be prepared by conventional methods from solutions containing compounds of the various elements, from solutions of the same pure elements, or from the mixture of both, by adjusting the desired atomic ratios. The above mentioned solutions are preferably watery solutions.

The procedure to prepare the multimetallic mixed oxides catalyst comprises at least the following stages:

1.—A first stage in which the different metallic precursors are mixed and the pH of the solutions can be adjusted.
2.—The second step involves the set-up of the preparation conditions of the metallic precursor mixture of the previous step to produce a solid either by hydrothermal or heat treatment process.
3.—The third stage involves the drying the solid obtained in the second step.
4.—The fourth stage involves the thermal treatment procedure of the dried solid, in order to get an activated solid, which can be used as catalyst for the oxidative dehydrogenation of ethane to ethylene.

In the first stage, the metallic precursors may be: pure metallic elements, metallic salts, metallic oxides, metallic hydroxides, metallic alkoxides, mineral acids, and/or mixtures thereof. The pH of the mixture of multimetallic mixed oxides of the first stage may be adjusted with organic or inorganic bases or mineral acids, such as, ammonia, $H_2SO_4$, $HNO_3$, HCl or mixture of thereof.

According to one preparation procedure, after the second stage the mixture is subject to hydrothermal treatment, as second step, and kept between 100-200° C. for 12-150 hours. After the second stage the mixture is heat treated at a temperature ranging from 50-100° C. Then the mixture is subjected to evaporation process to remove water.

In the "doping" preparation procedure, in which doping elements are incorporated into the multimetallic mixed oxides of the first stage, such incorporated elements include Nb, Cu, W, Bi, Sn, Ti, Fe, Co, Ni, Cr, Ga, Zr, rare earth elements, alkali metal or alkaline earth metal, as salts, oxides, hydroxides, or alkoxides, pure or as mixtures of thereof. Next, the mixture is heat treated at a temperature ranging from 50-100° C. and subjected to evaporation process to remove water.

The multimetallic mixed oxide mixture, prepared in the second stage either by hydrothermal or heat treatments, is washed or dried at 80-120° C., as a third step.

The dried solids, obtained in the third step, are activated by thermal treatments at temperatures ranging from 150-350° C. under oxidant and/or reducing and/or inert atmosphere for 1 to 5 hours; and then thermally treated at temperatures ranging from 150 to 700° C. under an oxidant and/or inert flow, preferably nitrogen, for 1 to 5 hours.

The washed and dried solids prepared in the second stage either by hydrothermal or heat treatments are thermally treated at temperature ranging from 150 to 700° C. Then doping solutions containing elements, such as, Nb, Cu, W, Bi, Sn, Ti, Fe, Co, Ni, Cr, Ga, Zr, rare earth elements, alkali metal or alkaline earth metal, as salts, oxides, hydroxides, or alkoxides, pure or as mixtures of thereof; are mixed with the thermally treated solid. The promoted materials obtained in this way are dried at 80-120° C. Dried solids are activated by thermal treatments at temperatures ranging from 150-350° C., preferably 160-300° C., under oxidant and/or reducing and/or inert atmosphere for 1 to 5 hours; and then thermally treated at temperatures ranging from 150 to 700° C., preferably 550 to 650° C. under an oxidant and/or inert flow, preferably nitrogen, for 1 to 5 hours.

According to the process for preparing the catalyst of the present invention in which a structure-directing compound is added into the multimetallic mixed oxide mixture prepared in the first step, such organic species are used as a template, or structure directing agent or as a modifier of the oxidation state of metallic elements forming the solid. When such organic compound is added into the multimetallic mixed oxide mixture, the mixture is subjected to either hydrothermal or heat treatment, as second step, at a temperature between 100-200° C., preferably between 150-180° C. for 12-48 hours. As third step, the produced solid is washed and dried at 80-120° C. The organic structure-directing compound may be primary amines, secondary amines, tertiary amines, ammonia, tetra-methyl ammonium or hydrazine. Preferably, methylamine, dimethyl amine, tri-methyl amine, diethyl amine, or mixtures thereof are utilized. The quantity of amine that is incorporated into the multimetallic mixed oxide mixture depends upon the amount of Mo that the catalyst will contain. The atomic ratio of nitrogen (in the amine) to Mo in the multimetallic mixed oxide mixture lies in the 0.0001-5.0 range.

If hydrazine is added to the multimetallic mixed oxide mixture, as the structure-directing compound, it should be used in a molar ratio of $N_2H_4$/Mo within the range 0.001 to 2.0, preferably from 0.01 and 1.0.

In the first mixing stage, the metallic precursors are molybdenum, vanadium and antimony, which can be added as pure metallic elements, or metallic salts, or metallic oxides, or metallic hydroxides, or metallic alkoxides or mineral acids or as mixtures of them. Hence, sulfates, oxalates, halides or nitrates can be used as metallic salts, preferably halides and sulfates. The term "metallic precursor" is intended to include any such form of molybdenum, vanadium and antimony.

Molybdenum may be added in the mixing stage preferably in the form of ammonium molybdate, molybdic acid, ammonium hepta-molybdate or molybdenum oxide. Vanadium can be incorporated during the mixing stage as well, preferably in the form of ammonia vanadate, vanadyl sulfate, vanadium oxide, vanadyl oxalate or vanadyl chloride. Antimonium, in turn, can be also added during the mixing stage preferably as antimonium oxide, antimonium sulfate, antimonium oxalate, antimonium chloride, antimonium bromide, antimonium iodide, antimonium fluoride or metallic antimonium. In the said compounds, antimonium can be in the form of Sb (III), Sb(V) or Sb (O), preferably as compound of Sb (III).

The doping elements Nb, Cu, W, Bi, Sn, Ti, Fe, Co, Ni, Cr, Ga, Zr, rare earth metals, alkali metal or alkaline rare earths metals, can be added in the form of oxides, hydroxides or alkoxides, pure or as a part of a mixture of two or more elements. As a metals source, metallic sulfates, oxalates, halides or nitrates can be utilized, more preferably halides and sulfates.

Hydrazine, in turn, can be also added during the mixing stage or once all the different metallic compounds have been already incorporated.

The mixing stage can be followed by a holding period in a reactor either in static mode or under stifling. The period of time, statics or under stifling, can be conducted at atmospheric pressure or under pressure. After concluding the mixing stage, the formation of the solid precursor of the multimetallic mixed oxide catalyst is conducted either by hydrothermal or heat thermal process.

The third stage, for the heat thermal process, can be performed by means of conventional methods, that is evaporation in an oven, or vacuum drying, or spray drying, and/or mixture of thereof.

In the particular case of preparing said materials through a hydrothermal procedure, the temperature and time of reaction synthesis have an important influence on the physicochemical properties of the solid. Hence, the temperature of synthesis is ranging from 100 to 200° C. and, preferably between 150 and 180° C. The time of synthesis lies, preferably, within the 6-150 hours range, and more specifically, from 12 to 48 hours.

In an alternative preparation of the procedure disclosed in the present invention, wherein into the mixture of multimetallic mixed oxides of molybdenum, vanadium and antimony are incorporated as metallic oxides on a support, such as, silica, silica gel, amorphous silica, zirconium oxide, silicon carbide, alumina, titanium oxide, cordierite, kaolin, alumino-silicates or a mixture thereof.

In an alternative preparation of the procedure disclosed in the present invention, wherein the amount of metallic oxides used as support, such as, silica, silica gel, amorphous silica, zirconium oxide, silicon carbide, alumina, titanium oxide, cordierite, kaolin, alumino-silicates, or a mixture thereof, may range from 20 to 70 wt. %.

In an alternative preparation of the procedure disclosed in the present invention, wherein an oxidant agent, such as $H_2O_2$, is added to the mixture of multimetallic mixed oxides of molybdenum, vanadium and antimony and the support selected, in order to adjust the oxidation state of cations. The final mixture is heat treated at a temperature ranging from 50-100° C., preferably between 70-90° C., and then it is subjected to evaporation process to remove water. As final step, the produced solid is washed and dried at 80-120° C.

Activation Process of Multimetallic Mixed Oxides

The activation process for the dried multimetallic mixed oxides is performed by thermal treatments at temperatures ranging from 150-350° C., preferably from 160-300° C. under oxidant and/or reducing and/or inert atmosphere for 1 to 5 hours, preferably 2 hours; and then thermally treated at temperatures ranging from 150 to 700° C., preferably from 550-650° C. under an oxidant and/or inert flow, preferably nitrogen, for 1 to 5 hours, preferably 2 hours.

In the activation process of the dried solids obtained in the third stage, the oxidizing agents may be oxygen, air, $CO_2$, nitrous oxide, ozone or mixtures thereof, more preferably oxygen and air.

Alternatively, the activation of the dried solids obtained in the third stage may be conducted with inert agents including nitrogen, argon, helium, krypton, neon, xenon or mixtures thereof, more preferably nitrogen.

Likewise, the activation process of the dried solids obtained in the third stage may be conducted with reducing agents including hydrogen, CO, alcohols, $H_2O_2$, light hydrocarbons such as methane, or mixtures thereof.

Once available in the thermally-treated form, the catalyst prepared in accordance to the procedure described in the present invention is suitable to be used for the oxidative dehydrogenation of ethane to produce ethylene.

Application of Activated Multimetallic Mixed Oxides as Catalysts for Oxidative Dehydrogenation of Ethane to Ethylene The oxidative dehydrogenation of ethane to produce ethylene involves contacting ethane or ethane mixed with other light hydrocarbons, with an oxidant agent and/or an inert agent, using as catalyst the activated multimetallic mixed oxide solid. The feedstock for conversion of ethane, or ethane mixed with other light hydrocarbons, to ethylene; preferably utilize light hydrocarbons restricted to $C_1$ to $C_4$ in which their content is lower than 15 volume % with respect to ethane. Conversion of ethane, or ethane mixed with other light hydrocarbons, to ethylene, utilizes an oxidizing agent which may be oxygen, air, $CO_2$, nitrous oxide, ozone or mixtures thereof, more preferably oxygen and air. Ethane, or ethane mixed with other light hydrocarbons, may include an inert agent, which can be nitrogen, argon, helium, krypton, neon, xenon or mixtures of thereof, more preferably nitrogen. When the oxidative dehydrogenation of ethane to ethylene is conducted in the gas phase, it is carried out in the presence of water vapor. The water content can vary from 0.0001 to 80 mole %, more preferably between 20 and 60 mole %. The catalyst of the present invention exhibits high ethane conversion of and high ethylene selectivity of higher than 92%, at moderate reaction temperatures <500° C., and atmospheric pressure, without the formation of acetic acid and/or other oxygenated hydrocarbons. The conversion of ethane, or ethane mixed with other light hydrocarbons, to ethylene, may be performed in fixed-bed multi-tubular or fluidized-bed reactors at atmospheric pressure (between about 0.77 and 1 atmosphere) or under pressure as is conventional at a reaction temperature of from about 250 to 550° C., preferably between 300 and 480° C., and more preferably within the range 350-450° C. A space-time corresponding to the ratio of the catalyst mass to the inlet molar flow rate of ethane ($W/F_{ethane}^°$) was spanned in the range 10 and 800 $g_{cat}$ h (mol)$^{-1}$, preferably within the 20-600 $g_{cat}$ h (mol)$^{-1}$ range, and more preferably between 30 and 350 $g_{cat}$ h (mol)$^{-1}$ may be utilized. The catalysts of the present invention provide high ethane conversion, ethylene selectivity and ethylene yield. For example, $MoV_hSb_iA_jO_x$ catalysts display an ethane conversion higher than 86 mole % and the ethylene selectivity can be higher than 95 mole %, at reaction temperatures varied from 250 to 550° C., and at atmospheric pressure; wherein the space-time corresponding to the ratio of the catalyst mass to the inlet molar flow rate of ethane ($W/F_{ethane}^°$) was spanned in the range 10 and 800 $g_{cat}$ h (mol)$^{-1}$. The use of activated $MoV_hSb_i$ catalyst can provide an ethylene selectivity higher than 92%, ethane conversion is higher than 86% with the reaction temperatures ranges from 420 to 540° C., under an operating pressure comprised between 0.8 to 1 atm. The $W/F_{ethane}^°$ was spanned in the 80 to 160 $g_{cat}$ h (mol)$^{-1}$ range.

An activated $MoV_hSb_i$ catalyst, prepared according to the claims 1 to 6 wherein the ethylene yield is higher than 70% at reaction temperatures ranging from 420 to 540° C., under an operating pressure comprised between 0.8 to 1 atm. and the $W/F_{ethane}^°$ spanned in the 80 to 160 $g_{cat}$ h (mol)$^{-1}$ range. The use of activated $MoV_hSb_iA_j$ catalysts can provide ethylene selectivity higher than 92%, ethane conversion higher than 84% and the reaction temperatures ranges from 420 to 450° C., under an operating pressure comprised between 0.8 to 1 atm, with a $W/F_{ethane}^°$ of 160 $g_{cat}$ h (mol)$^{-1}$. Likewise, such catalyst can provide an ethylene yield higher than 71%, at reaction temperatures ranging from 420 to 450° C., under an operating pressure comprised between 0.8 to 1 atm. The $W/F_{ethane}^°$ was 160 $g_{cat}$ h (mol)$^{-1}$. The use of activated $MoV_hSb_i$ catalyst provides ethylene selectivity higher than 93%, ethane conversion is higher than 75% at reaction temperatures from 390 to 470° C., under an operating pressure comprised between 0.8 to 1 atm. The $W/F_{ethane}^°$ was spanned in the 80 to 160 $g_{cat}$ h (mol)$^{-1}$ range. Likewise, such catalyst can provide ethylene yield higher than 62%, at reaction temperatures ranging from 390 to 470° C., under an operating pressure comprised between 0.8 to 1 atm. The $W/F_{ethane}^°$ was spanned in the 80 to 160 $g_{cat}$ h (mol)$^{-1}$ range.

The use of activated $MoV_hSb_iA_j$ catalyst supported over a metal oxide results in ethylene selectivity higher than 95% and ethane conversion higher than 71% using reaction temperatures from 430 to 460° C., under an operating pressure comprised between 0.8 to 1 atm. The $W/F_{ethane}^°$ is in the 170 to 320 $g_{cat}$ h (mol)$^{-1}$ range. An activated $MoV_hSb_iA_j$ catalyst supported over a metal oxide can provide an ethylene yield higher than 63%, at reaction temperatures ranging from 430 to 460° C., under an operating pressure comprised between 0.8 to 1 atm. The $W/F_{ethane}^°$ was in the 170 to 320 $g_{cat}$ h (mol)$^{-1}$ range. Thus, the catalysts of the present invention provide an ethane conversion higher than 86 mole % and the ethylene selectivity can be higher than 95 mole %, at moderate reaction temperatures <500° C., and at atmospheric pressure as indicated by the following Examples.

EXAMPLES

Once the basic aspects related to the present invention have been described a series of examples are offered to illustrate specific embodiments; notwithstanding, the invention should not be considered to be limited to said. Room temperature is defined herein after as temperature ranging from 10 and 40° C. The results of the catalytic tests, associated to examples here presented, were obtained at atmospheric pressure, which is here defined as a pressure ranging between 0.77 and 1 atmosphere.

Examples 1 to 14 are related to catalyst prepared by means of the so-called hydrothermal method.

Example 1

11.7 grams of tetra-hydrated ammonium hepta-molybdate and 2.7 grams of antimonium sulfate are dissolved in 85 grams of distilled water at 80° C. In parallel, a solution is prepared with 4.0 grams of vanadyl sulfate in 17 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 1, with the atomic ratio $Mo_{1.0}V_{0.36}Sb_{0.15}$. In a further stage, it is catalytically tested in quartz made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 2

10.7 grams of tetra-hydrated ammonium hepta-molybdate and 3.3 grams of antimonium bromide are dissolved in 78 grams of distilled water at 80° C. In parallel, a solution is prepared with 3.6 grams of vanadyl sulfate in 15 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is denoted as Catalyst 2, with the atomic ratio $Mo_{1.0}V_{0.36}Sb_{0.15}$. In a further stage, it is catalytically tested in a quartz-made fixed-bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 3

12.3 grams of tetra-hydrated ammonium hepta-molybdate and 2.4 grams of antimonium chloride are dissolved in 90 grams of distilled water at 80° C. In parallel, a solution is prepared with 4.1 grams of vanadyl sulfate in 17 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 3, with the atomic ratio $Mo_{1.36}Sb_{0.15}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 4

9.0 grams of tetra-hydrated ammonium hepta-molybdate and 2.1 grams of antimonium sulfate are dissolved in 79 grams of distilled water at 80° C. and then, this solution is acidified with 4.0 ml of $H_2SO_4$ 1M (pH=2.0). In parallel, another solution is prepared with 3.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stifling, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is denoted as Catalyst 4, with the atomic ratio $Mo_{1.0}V_{0.36}Sb_{0.15}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 5

18.1 grams of tetra-hydrated ammonium hepta-molybdate and 4.1 grams of antimonium sulfate are dissolved in 132 grams of distilled water at 80° C. and, the resulting solution is acidified with 8.5 ml of $H_2SO_4$ 1M (pH=2.0). In parallel, another solution is prepared with 6.0 grams of vanadyl sulfate in 25 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 1 day. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 5, with the atomic ratio $Mo_{1.0}V_{0.36}Sb_{0.15}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 6

8.9 grams of tetra-hydrated ammonium hepta-molybdate and 2.7 grams of antimonium bromide are dissolved in 141 grams of distilled water at 80° C. In parallel, a solution is prepared with 3.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 6, with the atomic ratio $Mo_{1.36}Sb_{0.15}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 7

17.1 grams of tetra-hydrated ammonium hepta-molybdate and 5.3 grams of antimonium bromide are dissolved in 125 grams of distilled water at 80° C. In parallel, a solution is prepared with 5.7 grams of vanadyl sulfate in 24 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 2 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 7, with the atomic ratio $Mo_{1.36}Sb_{0.15}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 8

Figure 1:
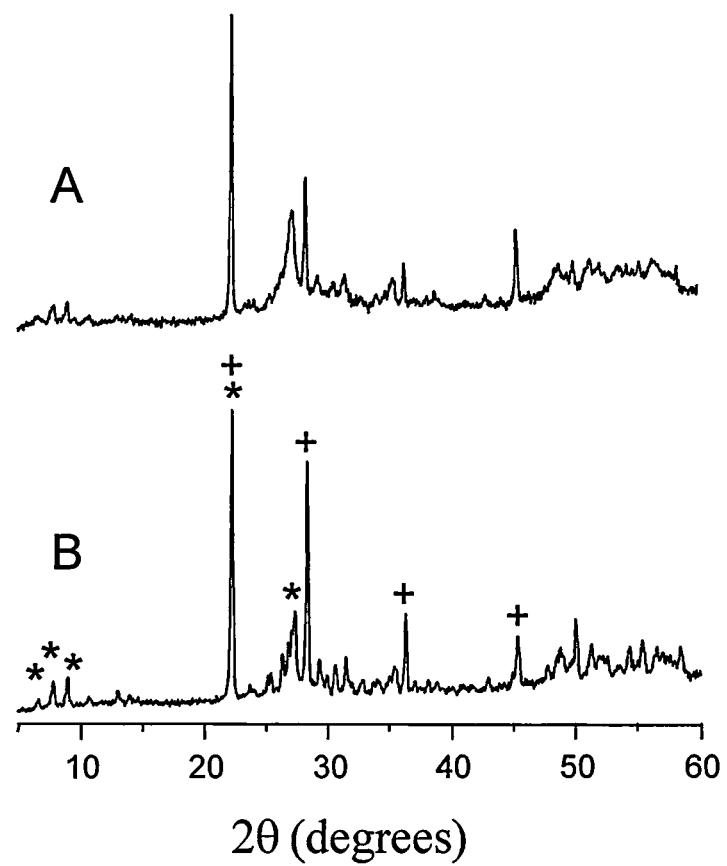
FIG. 1 are XRD spectra of catalyst prepared according to Example 8. (A) Solid dried at 100° C., and (B) Solid thermally-treated under nitrogen atmosphere at 600° C. Symbol [*] denotes phase M1 and [+] phase M2.

10.8 grams of tetra-hydrated ammonium hepta-molybdate and 3.3 grams of antimonium bromide are dissolved in 79 grams of distilled water at 80° C. In parallel, a solution is prepared with 3.6 grams of vanadyl sulfate in 15 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stifling, at 175° C. for 1 day. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 8 with the atomic ratio $Mo_{1.0}V_{0.36}Sb_{0.15}$. The X-ray diffraction spectra of the catalyst, (A) dried at 100° C. and (B) thermally treated at 600° C. under nitrogen flow are shown in FIG. 1. Scanning Electron Microscopy (SEM) images of the catalyst, dried at 100° C., are presented in FIG. 11; it is observed clearly the well ordering of crystallites, which are arranged forming cavities with suitable porosity to enhance the molecular traffic. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 9

17.5 grams of tetra-hydrated ammonium hepta-molybdate and 5.4 grams of antimonium bromide are dissolved in 127 grams of distilled water at 80° C. In parallel, a solution is prepared with 5.8 grams of vanadyl sulfate in 25 grams of distilled water at room temperature. The second solution is added slowly to the first one at room temperature under constant stifling and then 0.2 grams of potassium hydrogen carbonate are incorporated into the new solution. The resulting mixture is next transferred to a Teflon coated stainless-steel autoclave. Nitrogen is bubbled for 5 minutes in the mixture to remove the air contained inside the autoclave. Then, the autoclave is maintained, without stifling, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. The solid resulting from this example is coded as Catalyst 9 with the atomic ratio $Mo_{1.0}V_{0.36}Sb_{0.15}K_{0.02}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 10

18.1 grams of tetra-hydrated ammonium hepta-molybdate and 5.5 grams of antimonium bromide are dissolved in 132 grams of distilled water at 80° C. In parallel, a solution is prepared with 6.0 grams of vanadyl sulfate in 25 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. Separately, 0.01 grams of potassium hydrogen carbonate are dissolved in 3.1 grams of water at room temperature to produce a solution that is added to 7.8 g of the solid previously obtained. The suspension resulting from the previous stage is filtered and the solid obtained is washed with distilled water, dried at 100° C. and then treated thermally at 600° C. for 2 hours under nitrogen flow. This thermally-treated sample is designated Catalyst 10 with the atomic ratio $Mo_{1.0}V_{0.36}Sb_{0.15}K_{0.002}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 11

18.1 grams of tetra-hydrated ammonium hepta-molybdate and 5.5 grams of antimonium bromide are dissolved in 132 grams of distilled water at 80° C. In parallel, a solution is prepared with 6.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. Separately, 0.02 grams of copper (II) sulfate are dissolved in 3.1 grams of water at room temperature to produce a solution that is added to 7.8 g of the solid previously obtained. The suspension resulting from the previous stage is filtered and the solid obtained is washed with distilled water, dried at 100° C. and then treated thermally at 600° C. for 2 hours under nitrogen flow. This thermally-treated sample is denoted as Catalyst 11 with the atomic ratio $Mo_{1.0}V_{0.36}Sb_{0.15}Cu_{0.003}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 12

18.1 grams of tetrahydrated ammonium hepta-molybdate and 5.5 grams of antimonium bromide are dissolved in 132 grams of distilled water at 80° C. In parallel, a solution is prepared with 6.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. Separately, 0.02 grams of niobium oxalate are dissolved in 3.1 grams of water at room temperature to produce a solution that is added to 7.8 g of the solid previously obtained. The suspension resulting from the previous stage is filtered and the solid obtained is washed with distilled water, dried at 100° C. and then treated thermally at 600° C. for 2 hours under nitrogen flow. This thermally-treated sample is designated Catalyst 12 with the atomic ratio $Mo_{1.0}V_{0.36}Sb_{0.15}Nb_{0.003}$. In a further stage, it catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 13

18.1 grams of tetra-hydrated ammonium hepta-molybdate and 5.5 grams of antimonium bromide are dissolved in 132 grams of distilled water at 80° C. In parallel, a solution is prepared with 6.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. Separately, 0.03 grams of ammonium meta-tungstate are dissolved in 3.1 grams of water at room temperature to produce a solution that is added to 7.8 g of the solid formerly obtained. The suspension resulting from the previous step is filtered and the solid obtained is washed with distilled water, dried at 100° C. and then treated thermally at 600° C. for 2 hours under nitrogen flow. This thermally-treated sample is designated Catalyst 13 with the atomic ratio $Mo_{1.0}V_{0.36}Sb_{0.15}W_{0.002}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

Example 14

18.1 grams of tetra-hydrated ammonium hepta-molybdate and 5.5 grams of antimonium bromide are dissolved in 132 grams of distilled water at 80° C. In parallel, a solution is prepared with 6.0 grams of vanadyl sulfate in 13 grams of distilled water at room temperature. The second solution is added slowly to the first one at room temperature under constant stifling. The resulting mixture is then transferred to a Teflon coated stainless-steel autoclave. Nitrogen is bubbled for 5 minutes in the mixture to remove the air contained inside the autoclave. Then, the autoclave is maintained, without stirring, at 175° C. for 4 days. Autoclave is subsequently cooled down to room temperature. The content of the autoclave is filtered and, next, the solid fraction is recovered and washed with distilled water. Subsequently, the solid is dried at 100° C. and then treated thermally at 600° C. for 2 hours under nitrogen flow. Separately, 0.03 grams of tin (II) sulfate are dissolved in 3.1 grams of water at room temperature to produce a solution that is added to 7.8 g of the solid formerly obtained. The suspension resulting from the previous step is filtered and the solid obtained is washed with distilled water, dried at 100° C. and then treated thermally at 600° C. for 2 hours under nitrogen flow. This thermally-treated sample is designated Catalyst 14 with the atomic ratio $Mo_{1.0}V_{0.36}Sb_{0.15}Sn_{0.003}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 1.

As seen in the XRD spectra of FIG. 17, the catalysts of Examples 10-14 possess M1, M2 and $MoO_3$ crystalline phases.

Examples 15 to 22 correspond to the preparation of catalysts by means of the heat thermal method.

Example 15

3.6 grams of tetra-hydrated ammonium hepta-molybdate and 0.9 grams of antimonium sulfate are dissolved in 63 grams of distilled water at 80° C. under continuous stirring for around 1 hour. The previous solution is acidified by adding 2.3 ml of $HNO_3$ 1M (pH=2.2) followed by the incorporation of 0.6 grams of ammonium metavanadate. The resulting mixture is stirred for several minutes (solution A). In parallel, 0.5 grams of niobium oxalate are dissolved in 18 grams of distilled water at 80° C. (solution B). Subsequently, solution B is slowly added to solution A at room temperature under continuous stifling. The water constituting the new solution is removed by evaporation under vacuum at 50° C. in a rotavapor. The resulting solid is dried at 100° C., then treated thermally at 280° C. under nitrogen flow and finally treated thermally at 600° C. for 2 hours under nitrogen flow. The solid sample produced in this example is referred to as Catalyst 15 with the atomic ratio $Mo_{1.0}V_{0.25}Sb_{0.16}Nb_{0.06}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 16

2.5 grams of tetra-hydrated ammonium hepta-molybdate and 0.6 grams of antimonium sulfate are dissolved in 43 grams of distilled water at 80° C. under continuous stirring for around 1 hour. The previous solution is acidified by adding 1.6 ml of $HNO_3$ 1M (pH=2.4) followed by the incorporation of 0.4 grams of ammonium meta-vanadate. The resulting mixture is stirred for several minutes (solution A). In parallel, 0.4 grams of niobium oxalate are dissolved in 12 grams of distilled water at 80° C. (solution B). Subsequently, solution B is slowly added to solution A at room temperature under continuous stifling. The water constituting the new solution is removed by evaporation under vacuum at 50° C. in a rotavapor. The resulting solid is dried at 100° C., then treated thermally at 280° C. under air atmosphere and finally treated thermally at 600° C. for 2 hours under nitrogen flow. The solid sample produced in this example is designated Catalyst 16 with the atomic ratio $Mo_{1.0}V_{0.25}Sb_{0.16}Nb_{0.06}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 17

3.4 grams of tetrahydrated ammonium hepta-molybdate and 0.8 grams of antimonium sulfate are dissolved in 60 grams of distilled water at 80° C. under continuous stirring for around 1 hour. The previous solution is acidified by adding 1.3 ml of $H_2SO_4$ 1M (pH=2.5) followed by the incorporation of 0.6 grams of ammonium meta-vanadate and 4.7 ml of $HNO_3$ 1M (pH=2.4). The resulting mixture is stirred for several minutes (solution A). In parallel, 0.5 grams of niobium oxalate are dissolved in 17 grams of distilled water at 80° C. (solution B). Subsequently, solution B is slowly added to solution A at room temperature under continuous stifling. The water constituting the new solution is removed by evaporation under vacuum at 50° C. in a rotavapor. The resulting solid is dried at 100° C., then treated thermally at 280° C. under air atmosphere and finally treated thermally at 600° C. for 2 hours under nitrogen flow. The solid sample produced in this example is coded as Catalyst 17 with the atomic ratio $Mo_{1.0}V_{0.27}Sb_{0.16}Nb_{0.06}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 18

Figure 2:
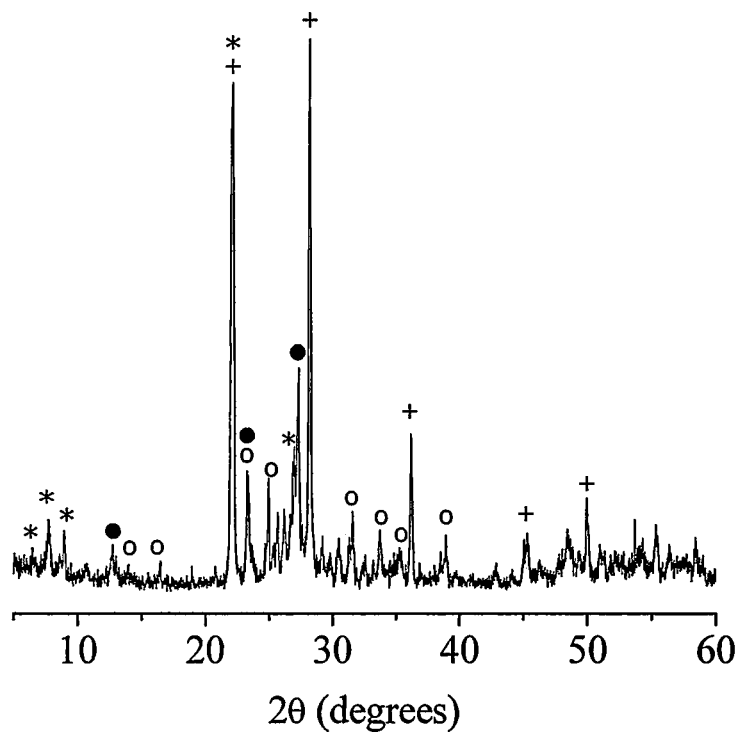
FIG. 2 is an XRD spectrum of catalyst prepared in accordance to Example 18 after thermal treatment under air atmosphere at 280° C. followed by thermal treatment under nitrogen flow at 600° C. Symbol [*] denotes phase M1, [+F] phase M2, [o] $(MoV_x)_{5-x}O_{14}$ and [●] $MoO_3$.

4.0 grams of tetra-hydrated ammonium hepta-molybdate and 0.9806 grams of antimonium sulfate are dissolved in 70 grams of distilled water at 80° C. under continuous stirring for around 1 hour. This solution is acidified by adding 1.2 ml of $H_2SO_4$ 1M (pH=2.5) followed by the incorporation of 0.6452 grams of ammonium meta-vanadate and 1.2 ml of HCl 1M (pH=2.5). The resulting mixture is stirred for several minutes (solution A). In parallel, 0.4211 grams of niobium oxalate are dissolved in 20 grams of distilled water at 80° C. The previous solution is cold down to room temperature and next 0.7 ml of $NH_4OH$ 1 M (pH=2.0) are added (solution B). Subsequently, solution B is slowly added to solution A at room temperature under continuous stirring. The water constituting the new solution is removed by evaporation under vacuum at 50° C. in a rotavapor. The resulting solid is dried at 100° C., then treated thermally at 280° C. under air atmosphere and finally treated thermally at 600° C. for 2 hours under nitrogen flow. The solid sample produced in this example is coded as Catalyst 18 with the atomic ratio $Mo_{1.0}V_{0.24}Sb_{0.16}Nb_{0.06}$. The X-ray diffraction pattern of the catalyst thermally treated at 280° C. under air atmosphere and then thermally treated at 600° C. under nitrogen flow is shown in FIG. 2. In a further stage, it is catalytically tested in a quartz-made fixed bed reactor using, as a feed, a gaseous mixture composed of ethane/oxygen/nitrogen with a nominal molar ratio of 9/7/83. The results of the catalytic activity testing with corresponding operating conditions in terms of temperature and space-time are displayed in Table 2.

Example 19

8.0 grams of tetra-hydrated ammonium hepta-molybdate and 2.62 grams of antimonium bromide are dissolved in 140 grams of distilled water at 80° C. under continuous stirring for ca. 1 hour. This solution is acidified by adding 1.3 ml of $H_2SO_4$ 1M (pH=2.5) followed by the incorporation of 1.27 grams of ammonium meta-vanadate and 4.7 ml of $HNO_3$ 1M (pH=2.5). The resulting mixture is stirred for several minutes (solution A). In parallel, 0.86 grams of niobium oxalate are dissolved in 40 grams of distilled water at 80° C. (solution B). Later, solution B is slowly added to solution A at room temperature under continuous stifling. The water constituting the new solution is removed by evaporation under vacuum at 50°

Figure 3:
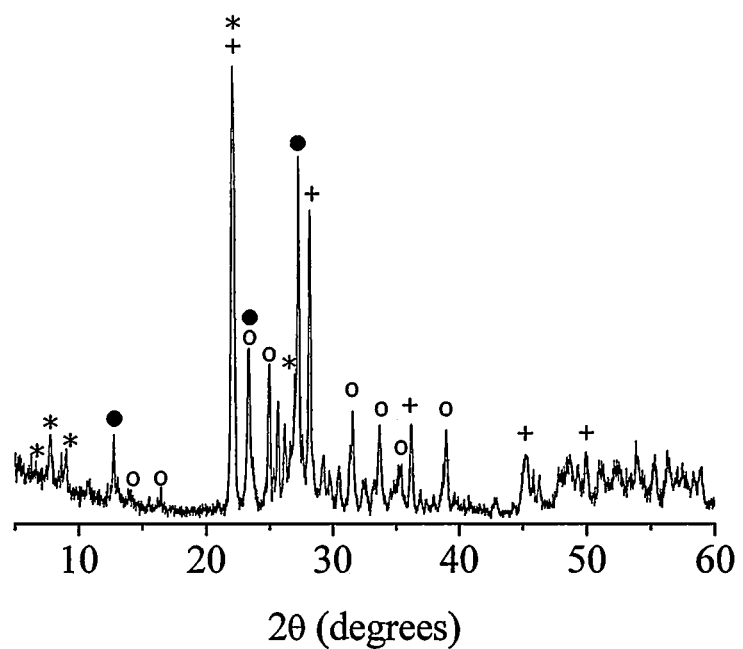
FIG. 3 is an XRD spectrum of catalyst prepared in accordance to Example 19 after thermal treatment under air atmosphere at 280° C. followed by thermal treatment under nitrogen flow at 600° C. Symbol [*] denotes phase M1, [+F] phase M2, [o] $(MoV_x)_{5-x}O_{14}$ and [●] $MoO_3$.

C. in a rotavapor. The resulting solid is dried at 100° C., and then treated thermally at 280° C. under air atmosphere and finally treated thermally at 600° C. for 2 hours under nitrogen flow. The solid sample produced in this example is coded as Catalyst 19 with the atomic ratio $Mo_{1.0}V_{0.24}Sb_{0.16}Nb_{0.06}$. The X-ray diffraction pattern of the catalyst thermally treated at 280° C. under air atmosphere and then thermally treated at 600° C. under nitrogen flow is shown in FIG. 3. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 20

Figure 4:
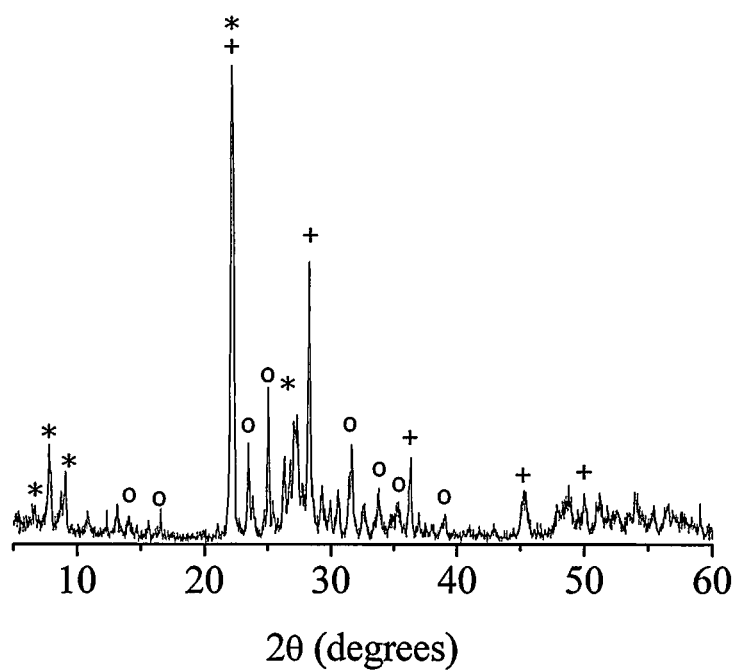
FIG. 4 is an XRD spectrum of catalyst prepared in accordance to Example 20 after thermal treatment under air atmosphere at 280° C. followed by thermal treatment under nitrogen flow at 600° C. Symbol [*] denotes phase M1, [+] phase M2, and [o] $(MoV_x)_{5-x}O_{14}$.

7.985 grams of tetra-hydrated ammonium hepta-molybdate and 1.642 grams of antimonium chloride are dissolved in 140 grams of distilled water at 72° C. under continuous stirring for around 1 hour. Then 1.295 grams of ammonium metavanadate are added to the previous solution followed by an acidification with 15.5 ml of HCl 1M (pH=1.5). The resulting mixture is stirred for several minutes (solution A). In parallel, 1.204 grams of niobium oxalate are dissolved in 40 grams of distilled water at 80° C. This solution is cooled down to room temperature and next 2.5 ml of NH4OH 1 M (pH=2.0) are added (solution B). Solution B is slowly added to solution A at room temperature under continuous stifling. The water constituting the new solution is removed by evaporation under vacuum at 60° C. in a rotavapor. The resulting solid is dried at 100° C., then treated thermally at 280° C. under air atmosphere and finally treated thermally at 600° C. for 2 hours under nitrogen flow. The solid sample produced in this example is coded as Catalyst 20 with the atomic ratio $Mo_{1.0}V_{0.25}Sb_{0.16}Nb_{0.06}$. The X-ray diffraction pattern of the catalyst thermally treated at 280° C. under air atmosphere and then thermally treated at 600° C. under nitrogen flow is shown in FIG. 4. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 21

Figure 5:
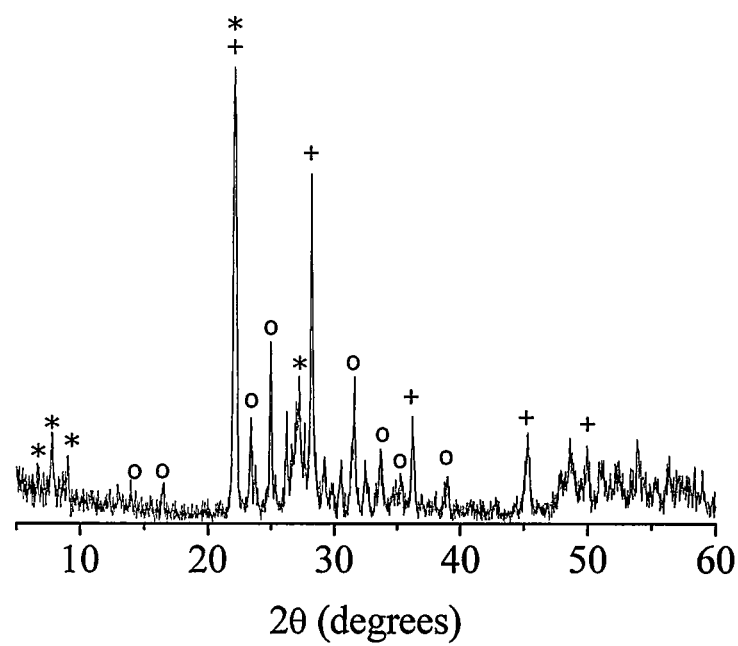
FIG. 5 is an XRD spectrum of catalyst prepared in accordance to Example 21 after thermal treatment under air atmosphere at 300° C. followed by thermal treatment under nitrogen flow at 600° C. Symbol [*] denotes phase M1, [+] phase M2, and [o] $(MoV_x)_{5-x}O_{14}$.

7.985 grams of tetra-hydrated ammonium hepta-molybdate and 1.642 grams of antimonium chloride are dissolved in 140 grams of distilled water at 70° C. under continuous stirring for around 1 hour. Then 1.295 grams of ammonium meta-vanadate are added to the previous solution followed by an acidification with 8.5 ml of HCl 1M (pH=1.8). The resulting mixture is stirred for several minutes (solution A). In parallel, 1.204 grams of niobium oxalate are dissolved in 40 grams of distilled water at 80° C. (solution B, pH=1.7). Later, solution B is slowly added to solution A at room temperature under continuous stirring. The water constituting the new solution is removed by evaporation under vacuum at 60° C. in a rotavapor. The resulting solid is dried at 100° C., then treated thermally at 300° C. under air atmosphere and finally treated thermally at 600° C. for 2 hours under nitrogen flow. The solid sample produced in this example is coded as Catalyst 21 with the atomic ratio $Mo_{1.0}V_{0.25}Sb_{0.16}Nb_{0.06}$. The X-ray diffraction pattern of the catalyst thermally treated at 300° C. under air atmosphere and then thermally treated at 600° C. under nitrogen flow is shown in FIG. 5. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

Example 22

Figure 6:
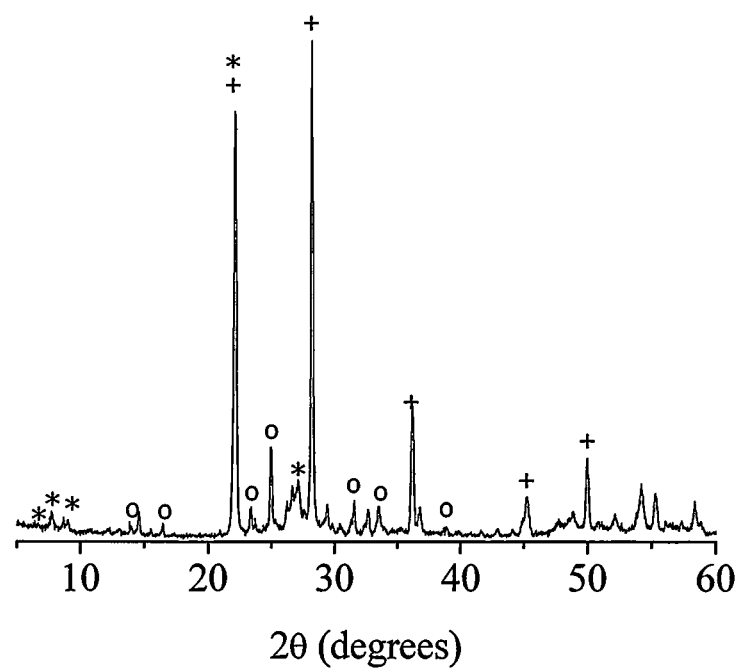
FIG. 6 is an XRD spectrum of catalyst prepared in accordance to Example 22 after a thermal treatment at 625° C. under nitrogen flow. Symbol [*] denotes phase M1, [+] phase M2, and [o] $(MoV_x)_{5-x}O_{14}$.

7.0 grams of tetra-hydrated ammonium hepta-molybdate are dissolved in 40 grams of distilled water at room temperature under continuous stifling and then 0.99 grams of antimonium trioxide and 0.80 grams of 50 wt. % solution of hydrogen peroxide are added. The resulting mixture is maintained under stirring at 80° C. for 1 hour until complete dissolution of the antimonium trioxide to produce solution A. In parallel, 1.4 grams of ammonium meta-vanadate are dissolved in 40 grams of distilled water at 80° C. (solution B). Also in parallel, 1.28 grams of niobium oxalate are dissolved in 20 grams of distilled water at 80° C. producing solution B. Later solution C is added to the solution produced after blending solution A and solution B to yield a new solution. Next, 0.136 grams of monohydrated hydrazine are added to this new solution at 80° C. stirring for 20 minutes. 2.55 ml of $H_2SO_4$ 10 wt. % (pH=4.7) are incorporated to mixture of the previous stage. The water that is part of this final mixture is vaporized by heating it at 200° C. The remaining solid is finally treated thermally at 625° C. for 2 hours under nitrogen flow. The thermally-treated solid is coded as Catalyst 22 with the atomic ratio $Mo_{1.0}V_{0.30}Sb_{0.17}Nb_{0.07}$. The X-ray diffraction pattern of the catalyst thermally treated at 625° C. under nitrogen flow is shown in FIG. 6. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 2.

The examples described from here on correspond to the preparation of the catalyst through the hydrothermal method involving the incorporation of amines in the synthesis.

Example 23

Figure 7:
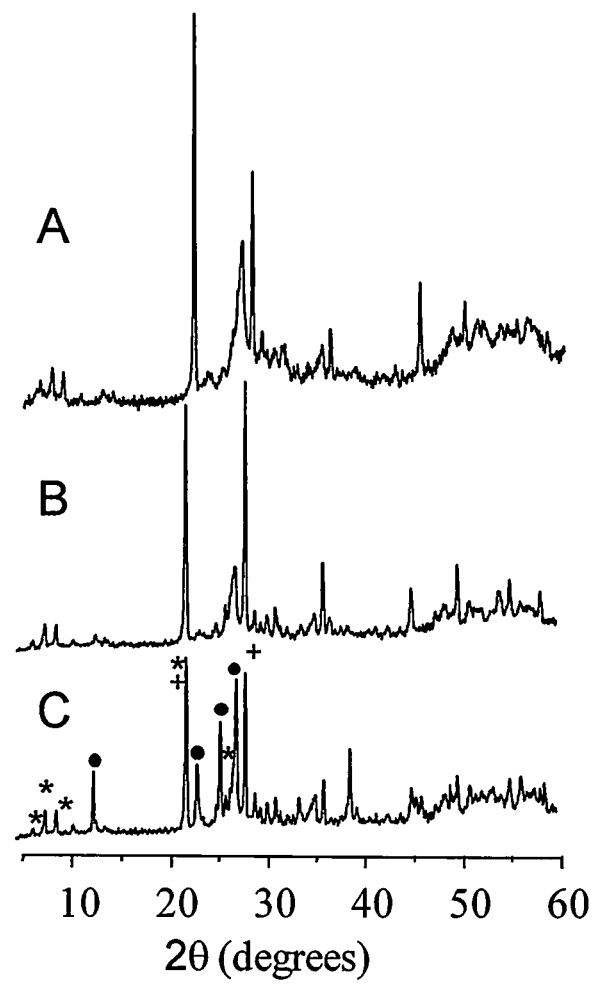
FIG. 7 are XRD spectra of catalyst prepared in accordance to Example 23. (A) Solid dried at 100° C., (B) Solid thermally-treated at 200° C. under air atmosphere followed by thermal treatment at 600° C. under nitrogen flow, and (C) Solid thermally-treated in air atmosphere at 250° C. followed by thermal treatment at 600° C. under nitrogen flow. Symbol [*] denotes phase M1, [+] phase M2, and [●] $MoO_3$.

6.9 grams of molybdic acid, 2.27 grams of methylamine hydrochloride ($CH_3NH_2HCl$) along with 1.58 g of antimonium sulfate are dissolved in 85 grams of distilled water at 80° C. In parallel, a second solution containing 2.29 g of vanadyl sulfate in 17 grams of water at room temperature is prepared. The second solution is slowly added to the first one at room temperature under stirring. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 250° C. under air atmosphere and finally treated thermally at 600° C. for 2 hours under nitrogen flow. The thermally-treated sample is designated Catalyst 23 with the atomic ratio $Mo_{1.38}Sb_{0.16}$. The X-ray diffraction patterns of the catalysts, (A) dried at 100° C., (B) thermally treated under air atmosphere at 200° C. and then thermally treated at 600° C. under nitrogen flow and (C) thermally treated under air atmosphere at 250° C. and then thermally treated at 600° C. under nitrogen flow, are shown in FIG. 7. Representative Scanning Electron Microscopy images of the catalyst, (Column A) dried at 100° C. and (Column B) thermally treated under air atmosphere at 250° C. and then thermally treated at 600° C. under nitrogen flow, are shown in FIG. 12. In FIG. 14, column A, in addition to Scanning Electron Microscopy images of the catalyst, is shown the elemental chemical analysis, of the selected zones, by Electron Dispersive Spectroscopy (EDS) technique (bottom part), of the catalyst thermally treated under air atmosphere at 250° C. and then thermally treated at 600° C. under nitrogen flow. Representative High-Resolution Transmission Electron Microscopy images of the catalyst are shown in FIG. 15, (A) crystal of M1 phase, and its corresponding electron nano-diffraction (END) pattern (right side), (B) crystal of M1 phase, and its corresponding END pattern (right side), and (C) crystal of $MoO_3$ phase, and its corresponding END pattern (right side). In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Example 24

Figure 8:
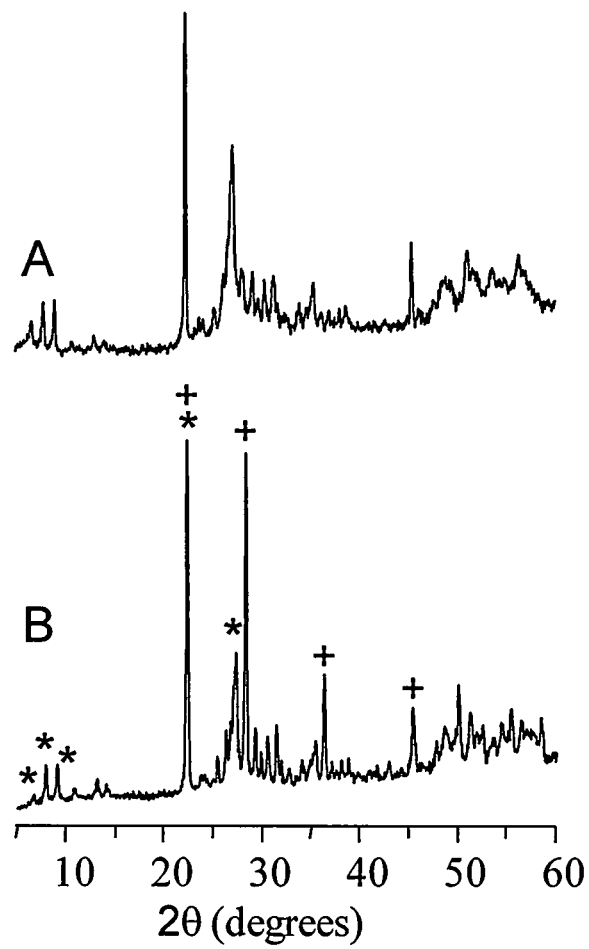
FIG. 8 are XRD spectra of catalyst prepared in accordance to Example 24. (A) Solid dried at 100° C., (B) catalyst after a thermal treatment at 200° C. under air atmosphere followed by a second thermal treatment at 600° C. Symbol [*] denotes phase M1, and [+] phase M2.

6.9 grams of molybdic acid, 2.73 grams of dimethylamine hydrochloride ($CH_3NH\ CH_3HCl$) along with 1.58 g of antimonium sulfate are dissolved in 85 grams of distilled water at 80° C. In parallel, a second solution containing 2.29 g of vanadyl sulfate in 17 grams of water at room temperature is prepared. The second solution is slowly added to the first one at room temperature under stirring. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 200° C. under air atmosphere and finally treated thermally at 600° C. for 2 hours under nitrogen flow. The thermally-treated sample is designated Catalyst 24 with the atomic ratio $Mo_{1.0}V_{0.38}Sb_{0.16}$. The X-ray diffraction patterns of the catalyst, (A) dried at 100° C., (B) thermally treated under air atmosphere at 200° C. and then thermally treated at 600° C. under nitrogen flow are shown in FIG. 8. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Example 25

Figure 9:
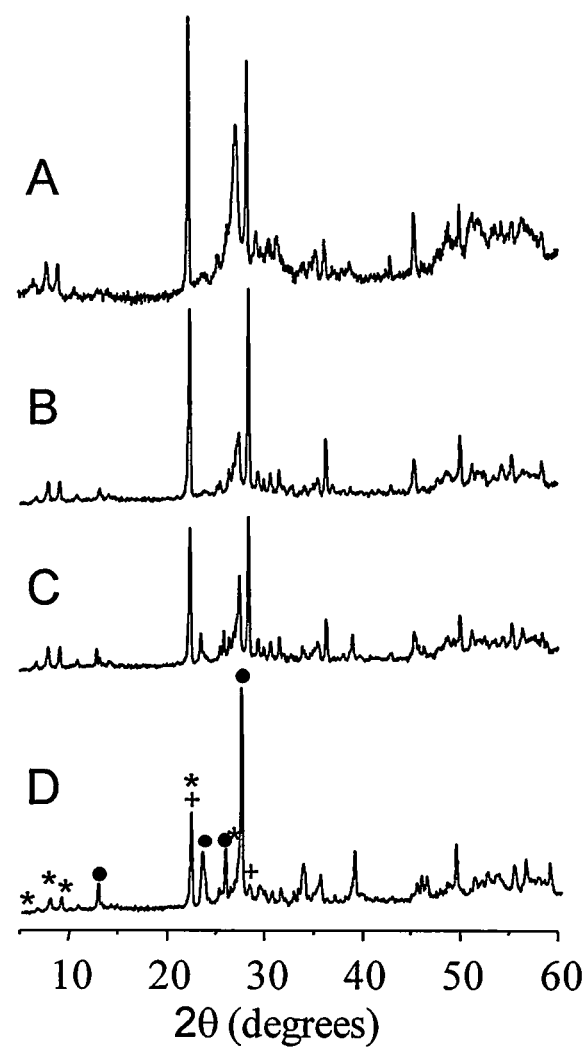
FIG. 9 are XRD spectra of catalyst prepared in accordance to Example 25. (A) Solid after drying at 100° C., (B) catalyst after a thermal treatment at 200° C. under air atmosphere followed by a second thermal treatment at 600° C. under nitrogen flow, (C) catalyst thermally-treated at 250° C. under air atmosphere followed by a second thermal treatment at 600° C. under nitrogen flow, and (D) Catalyst thermally-treated at 280° C. under air atmosphere followed by a second thermal treatment at 600° C. under nitrogen flow. Symbol [*] denotes phase M1, [+] phase M2, and [●] $MoO_3$.

6.9 grams of molybdic acid, 2.73 grams of ethylamine hydrochloride ($CH_3CH_2NH\ HCl$) and 1.58 g of antimonium sulfate are dissolved in 85 grams of distilled water at 80° C. In parallel, a second solution containing 2.29 g of vanadyl sulfate in 17 grams of water at room temperature is prepared. The second solution is slowly added to the first one at room temperature under stifling. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 250° C. under air atmosphere and finally treated thermally at 600° C. for 2 hours under nitrogen flow. The thermally-treated sample is designated Catalyst 25 with the atomic ratio $Mo_{1.0}V_{0.38}Sb_{0.16}$. The X-ray diffraction patterns of the catalyst, (A) dried at 100° C., (B) thermally treated under air atmosphere at 200° C. and then thermally treated at 600° C. under nitrogen flow, (C) thermally treated under air atmosphere at 250° C. and then thermally treated at 600° C. under nitrogen flow and (D) thermally treated under air atmosphere at 280° C. and then thermally treated at 600° C. under nitrogen flow are shown in FIG. 9. In a further stage, is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Example 26

6.9 grams of molybdic acid, 2.73 grams of ethylamine hydrochloride ($CH_3CH_2NH\ HCl$) along with 1.58 g of antimonium sulfate are dissolved in 85 grams of distilled water at 80° C. In parallel, a second solution containing 2.29 g of vanadyl sulfate in 17 grams of water at room temperature is prepared. The second solution is slowly added to the first one at room temperature under stirring. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 200° C. under air atmosphere and finally treated thermally at 600° C. for 2 hours under nitrogen flow. The thermally-treated sample is designated Catalyst 26 with the atomic ratio $Mo_{1.0}V_{0.38}Sb_{0.16}$. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Example 27

Figure 10:
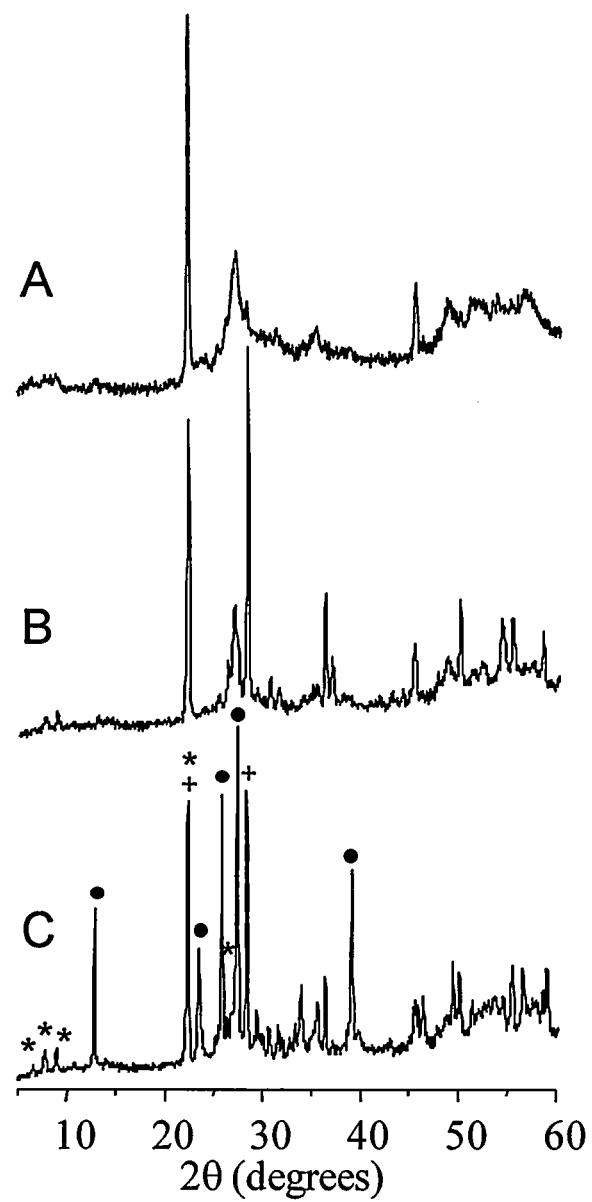
FIG. 10 are XRD spectra of catalyst prepared in accordance to Example 27. (A) Solid after drying at 100° C., (B) catalyst after a thermal treatment at 200° C. under air atmosphere followed by a second thermal treatment at 600° C. under nitrogen flow, (C) catalyst thermally-treated at 250° C.

6.9 grams of molybdic acid, 3.18 grams of trimethylamine hydrochloride [$(CH_3)_3NHCl$] along with 1.58 g of antimonium sulfate are dissolved in 85 ml of distilled water at 80° C. In parallel, a second solution containing 2.29 g of vanadyl sulfate in 17 grams of water at room temperature is prepared. The second solution is slowly added to the first one at room temperature under stifling. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 200° C. under air atmosphere and finally treated thermally at 600° C. for 2 hours under nitrogen flow. The thermally-treated sample is designated Catalyst 27 with the atomic ratio $Mo_{1.0}V_{0.38}Sb_{0.16}$. The X-ray diffraction patterns of the catalyst, (A) dried at 100° C., (B) thermally treated under air atmosphere at 200° C. and then thermally treated at 600° C. under nitrogen flow, (C) thermally treated under air atmosphere at 250° C. and then thermally treated at 600° C. under nitrogen flow are shown in FIG. 10. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Example 28

6.9 grams of molybdic acid, 3.18 grams of trimethyl-amine hydrochloride [$(CH_3)_3NHCl$] together with 1.58 g of antimonium sulfate are dissolved in 85 ml of distilled water at 80° C. In parallel, a second solution containing 2.29 g of vanadyl sulfate in 17 grams of water at room temperature is prepared. The second solution is slowly added to the first one at room temperature under stirring. The resulting mixture is further stirred for 30 minutes and, later, transferred into a Teflon coated stainless-steel autoclave. The mixture is bubbled with nitrogen for 5 minutes in order to displace out the air contained inside the autoclave. Then, the autoclave is maintained, without stirring, at 175° C. for 1 day. Autoclave is subsequently cooled down to room temperature, its content is filtered. The solid fraction is recovered and then subjected to washing with distilled water. The solid is later dried at 100° C., then treated thermally at 250° C. under air atmosphere and finally treated thermally at 600° C. for 2 hours under nitrogen flow. The thermally-treated sample is designated Catalyst 28 with the atomic ratio $Mo_{1.0}V_{0.38}Sb_{0.16}$. Representative Scanning Electron Microscopy images of the catalyst, (Column A) dried at 100° C. and (Column B) thermally treated under air atmosphere at 250° C. and then thermally treated at 600° C. under nitrogen flow, are shown in FIG. 13. In FIG. 14, column B, in addition to Scanning Electron Microscopy images of the catalyst, is shown the elemental chemical analysis, of the selected zones, by Electron Dispersive Spectroscopy technique (bottom part), of the catalyst thermally treated under air atmosphere at 250° C. and then thermally treated at 600° C. under nitrogen flow. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

The following example corresponds to the preparation of supported catalysts by the heat thermal method.

Example 29

8.0 grams of tetrahydrated ammonium hepta-molybdate, 1.2189 grams of ammonium meta-vanadate and 1.734 grams of antimonium oxide ($Sb_2O_3$) are dissolved in 32 grams of water at 100° C., the mixture was kept under stifling for 2 hours, after this, the solution was cooled at 50° C. Then, 7.96 grams of Silica gel, with a pore size of 60 Å and a surface area of 500 m$^2$/g was added and stirred for 30 min. Finally, 8 grams of diluted $H_2O_2$ (5 wt. %) was added and stirred for 1 hour (Solution A).

In parallel, a solution is prepared with 1.88 grams of niobium oxalate in 5 grams of water at 60° C. under stirring; the solution was cooled down at room temperature. The later solution is added slowly to the solution A at room temperature under constant stifling. The water constituting the new solution is removed by evaporation. The resulting solid is dried at 100° C., and then treated thermally at 600° C. for 2 hours under nitrogen flow. The solid sample produced in this example is composed by the 40 wt. % of $SiO_2$ and 60 wt. % of active phase with the atomic ratio $Mo_{1.0}V_{0.23}Sb_{0.26}Nb_{0.09}$, sample was labeled as Catalyst 29. In FIG. 16, in addition to Scanning Electron Microscopy images of the catalyst, is shown the elemental chemical analysis, of the selected zones, by Electron Dispersive Spectroscopy technique (right side), of the catalyst thermally treated at 600° C. under nitrogen flow. In a further stage, it is catalytically tested in a quartz-made fixed bed reactor using, as a feed, a gaseous mixture composed of ethane/oxygen/nitrogen with a nominal molar ratio of 9/7/84. The results of the catalytic activity testing with corresponding operating conditions in terms of temperature and space-time are displayed in Table 3.

Tables 1 to 3 show the catalytic performance results of multimetallic mixed oxides, which were prepared by several methodologies and with varied chemical compositions. Only, the most important parameters were included.

TABLE 1

Catalytic performance with corresponding operating conditions of the ODH-E over catalysts $MoV_hSb_iA_j$, which were prepared through the hydrothermal method.

| Example | Temperature, ° C. | $W/F_{ethane}^o$ $g_{cat}$ h $(mol)^{-1}$ | Ethane conversion, % | Ethylene selectivity, mol %. | Ethylene yield, mol % |
|---|---|---|---|---|---|
| Example 1 | 540 | 80 | 70 | 70 | 49 |
| Example 2 | 440 | 80 | 60 | 91 | 55 |
|  | 470 | 80 | 73 | 88 | 64 |
|  | 425 | 160 | 72 | 87 | 63 |
|  | 440 | 160 | 82 | 83 | 68 |
| Example 3 | 450 | 80 | 55 | 90 | 50 |
|  | 490 | 80 | 78 | 81 | 63 |
| Example 4 | 430 | 160 | 72 | 87 | 63 |
|  | 450 | 160 | 81 | 83 | 67 |
| Example 5 | 430 | 160 | 78 | 86 | 67 |
| Example 6 | 430 | 160 | 81 | 86 | 70 |
| Example 7 | 420 | 80 | 52 | 92 | 48 |
|  | 440 | 80 | 63 | 90 | 57 |
|  | 430 | 160 | 78 | 86 | 67 |
|  | 450 | 160 | 86 | 81 | 70 |
| Example 8 | 430 | 160 | 77 | 87 | 67 |
|  | 450 | 160 | 86 | 83 | 71 |
| Example 9 | 430 | 160 | 64 | 91 | 59 |
|  | 450 | 160 | 78 | 87 | 68 |
| Example 10 | 430 | 160 | 65 | 92 | 60 |
|  | 450 | 160 | 76 | 89 | 68 |
| Example 11 | 430 | 160 | 55 | 92 | 51 |
|  | 450 | 160 | 66 | 89 | 59 |
| Example 12 | 430 | 160 | 80 | 88 | 70 |
| Example 13 | 430 | 160 | 74 | 90 | 67 |
|  | 450 | 160 | 84 | 85 | 71 |
| Example 14 | 420 | 160 | 69 | 91 | 63 |

TABLE 2

Catalytic performance with corresponding operating conditions of the ODH-E over catalysts $MoV_hSb_iA_j$, which were prepared through the heat thermal method.

| Example | Temperature, °C | W/$F_{ethane}^o$ $g_{cat}$h (mol)$^{-1}$ | Ethane conversion, % | Ethylene selectivity, mol % | Ethylene yield, mol % |
|---|---|---|---|---|---|
| Example 15 | 440 | 160 | 37 | 93 | 34 |
| Example 16 | 450 | 160 | 45 | 90 | 41 |
|  | 470 | 160 | 57 | 87 | 50 |
| Example 17 | 440 | 160 | 47 | 92 | 43 |
| Example 18 | 440 | 70 | 29 | 95 | 28 |
| Example 19 | 440 | 70 | 23 | 93 | 21 |
| Example 20 | 440 | 70 | 30 | 93 | 28 |
| Example 21 | 440 | 70 | 33 | 91 | 30 |
|  | 440 | 140 | 50 | 89 | 45 |
| Example 22 | 440 | 70 | 23 | 90 | 21 |
|  | 480 | 70 | 50 | 83 | 42 |

TABLE 3

Catalytic performance with corresponding operating conditions of the ODH-E over catalysts $MoV_hSb_iA_j$ which were prepared through the hydrothermal method with the incorporation of amines in the synthesis.

| Example | Temperature, °C | W/$F_{ethane}^o$ $g_{cat}$h (mol)$^{-1}$ | Ethane conversion, % | Ethylene selectivity, mol % | Ethylene yield, mol % |
|---|---|---|---|---|---|
| Example 23 | 390 | 80 | 43 | 92 | 40 |
|  | 400 | 80 | 55 | 89 | 49 |
|  | 430 | 80 | 67 | 85 | 57 |
|  | 450 | 80 | 75 | 82 | 62 |
| Example 24 | 450 | 80 | 61 | 88 | 54 |
|  | 470 | 80 | 71 | 85 | 60 |
| Example 25 | 400 | 80 | 43 | 93 | 40 |
|  | 430 | 80 | 53 | 91 | 48 |
|  | 450 | 80 | 60 | 88 | 53 |
| Example 26 | 400 | 160 | 37 | 86 | 32 |
|  | 430 | 160 | 51 | 84 | 43 |
|  | 450 | 160 | 66 | 79 | 52 |
| Example 27 | 400 | 80 | 26 | 78 | 20 |
|  | 430 | 80 | 37 | 77 | 29 |
|  | 450 | 80 | 51 | 74 | 38 |
| Example 28 | 400 | 80 | 49 | 92 | 45 |
|  | 430 | 80 | 60 | 89 | 53 |
|  | 450 | 80 | 72 | 85 | 61 |
| Example 29 | 440 | 320 | 55 | 92 | 51 |
|  | 460 | 320 | 71 | 88 | 63 |
|  | 430 | 177 | 32 | 95 | 31 |
|  | 450 | 177 | 47 | 92 | 43 |

What is claimed is:

1. A process for the oxidative dehydrogenation of ethane to ethylene, which comprises contacting a feedstock comprising ethane and an oxidizing agent under oxidative dehydrogenation reaction conditions with a tellurium-free, multimetallic mixed oxide solid catalyst having the formula $$MoV_hSb_iO_x \quad (I)$$

wherein, h and i, respectively, are each between 0.001 and 4.0, the ratio i/h is between 0.3 and 10.0, and x represents the number determined by and consistent with the valence requirements of elements present in the multimetallic mixed oxide solid catalyst, said multimetallic mixed oxide solid catalyst having an orthorhombic M1 crystalline phase along with a pseudo-hexagonal M2 crystalline phase and an orthorhombic $MoO_3$ crystalline phase, and one or more additional crystalline phases, wherein a process of preparing said multimetallic mixed oxide solid catalyst comprises:

A) a process which comprises forming a tellurium-free mixture of molybdenum, vanadium and antimony metallic precursors and a compound selected from the group consisting of primary amines, secondary amines, tertiary amines, ammonia, tetra-methyl ammonium and hydrazine, and subjecting said tellurium-free mixture to hydrothermal condition at a temperature of 100-200° C. for 6-150 hours to obtain a solid, washing and drying said solid to obtain a dried solid, and thermally activating said dried solid to form a catalyst having the pseudo-hexagonal M2 crystalline phase and the orthorhombic $MoO_3$ crystalline phase in addition to the orthorhombic M1 crystalline phase, wherein said thermally activating includes a first thermal treatment at a temperature from about 150° C. to about 350° C. under an oxidizing, reducing or inert atmosphere for 1-5 hours, and thereafter a second thermal treatment at a temperature from about 150° C. to 700° C. under an oxidizing or inert atmosphere for 1 to 5 hours.

2. The process of claim 1, wherein the compound is selected from the group consisting of methylamine, dimethyl amine, tri-methyl amine, diethyl amine, or mixtures thereof.

3. The process of claim 2, wherein said solid is washed and dried at 80-120° C., prior to activation.

4. The process of claim 3, wherein said hydrothermal condition is at a temperature range of 150-180° C. for 12-48 hours.

5. A process for the oxidative dehydrogenation of ethane to ethylene, which comprises contacting a feedstock comprising ethane and an oxidizing agent under oxidative dehydrogenation reaction conditions with a tellurium-free, multimetallic mixed oxide solid catalyst having the formula $$MoV_hSb_iA_jO_x \quad (I)$$

wherein A represents Nb, W, Ga, Bi, Sn, Cu, Ti, Fe, Co, Ni, Cr, Zr, rare earth metals, alkali metals, alkaline earth metals, or a mixture thereof, h and i, respectively, are each between 0.001 and 4.0, the ratio i/h is between 0.3 and 10.0, and x represents the number determined by and consistent with the valence requirements of elements present in the multimetallic mixed oxide solid catalyst, said multimetallic mixed oxide solid catalyst having an orthorhombic M1 crystalline phase, a pseudo-hexagonal M2 crystalline phase, an orthorhombic $MoO_3$ crystalline phase, and one or more additional crystalline phases, wherein a process of preparing said multimetallic mixed oxide solid catalyst comprises the steps of forming a tellurium-free mixture of molybdenum, vanadium and antimony metallic precursors and thermally treating said tellurium-free mixture to form an MoVSb solid, doping said MoVSb solid with a solution containing metal cation of said metal A, as salts, oxides, hydroxides, or alkoxides to obtain a resulting mixture, drying the resulting mixture to obtain a solid and drying said solid to obtain a metal cation-doped MoVSb solid, and thermally activating the metal cation-doped MoVSb solid to form a catalyst having the pseudo-hexagonal M2 crystalline phase and the orthorhombic $MoO_3$ crystalline phase in addition to the orthorhombic M1 crystalline phase, where said thermally activating step includes a first thermal treatment at a temperature of from about 150° C. to about 350° C. under oxidizing and/or reducing atmosphere for 1 to 5 hours, and thereafter a second thermal treatment at a temperature of about 150° C. to about 700° C. under oxidizing or inert atmosphere for 1 to 5 hours, wherein said tellurium-free mixture includes a compound selected from the group consisting of primary amines, secondary amines, tertiary amines, ammonia, tetra-methyl ammonium and hydrazine, or mixtures thereof.

6. The process of claim 5, wherein the solution contains metal cation of Nb, W, Sn, Cu or K.

7. The process of claim 5, wherein said MoVSb solid is heated at a temperature range of from about 150° C. to about 600° C. prior to doping said MoVSb solid and then activating said metal cation-doped MoVSb solid at a temperature range of from about 150° C. to about 700° C. under an oxidizing or inert atmosphere for about 1 to 5 hours.

8. The process of claim 1, wherein said oxidative dehydrogenation reaction is carried out at a reaction temperature range of about from 250° C. to 550° C.

9. The process of claim 1, wherein said hydrothermal condition is at a temperature range of 150-180° C. for 12-48 hours.

10. The process for the oxidative dehydrogenation of ethane to ethylene, which comprises contacting a feedstock comprising ethane and an oxidizing agent under oxidative dehydrogenation reaction conditions with a tellurium-free, multimetallic mixed oxide solid catalyst, wherein the multimetallic mixed oxide has the formula $$MoV_hSb_iA_jO_x$$ 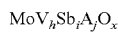

wherein A represents Nb, W, Ga, Bi, Sn, Cu, Ti, Fe, Co, Ni, Cr, Zr, rare earth metals, alkali metals, alkaline earth metals, or a mixture thereof, h and i, respectively, are each between 0.001 and 4.0, $0.0001 \leq j \leq 2.0$, the ratio i/h is between 0.3 and 10.0, and x represents the number determined by and consistent with the valence requirements of elements present in the multimetallic mixed oxide solid catalyst, said multimetallic mixed oxide solid catalyst having an orthorhombic M1 crystalline phase, along with a pseudo-hexagonal M2 crystalline phase and an orthorhombic $MoO_3$ crystalline phase, and one or more additional crystalline phases, and wherein a process of preparing said multimetallic mixed oxide solid catalyst comprises the steps of forming a tellurium-free mixture of molybdenum, vanadium and antimony metallic precursors and thermally treating said tellurium-free mixture to form an MoVSb solid, doping said MoVSb solid with a solution containing metal cation of said metal A to obtain an A metal cation-doped MoVSb solid, and thermally activating the A metal cation-doped MoVSb solid to form a catalyst having the pseudo-hexagonal M2 crystalline phase and the orthorhombic $MoO_3$ crystalline phase in addition to the orthorhombic M1 crystalline phase, wherein said tellurium-free mixture includes a compound selected from the group consisting of primary amines, secondary amines, tertiary amines, ammonia, tetra-methyl ammonium and hydrazine, or mixtures thereof.

11. The process of claim 10, wherein the solution contains metal cation of Nb, W, Sn, Cu or K.

12. The process of claim 10, wherein said MoVSb solid is heated at a temperature range of from about 150° C. to about 700° C. prior to doping said MoVSb solid and then activating said A metal cation-doped MoVSb solid at a temperature range of from about 150° C. to about 700° C. under an oxidizing or inert atmosphere for about 1 to 5 hours.

13. The process of claim 1, wherein the oxidative dehydrogenation reaction is conducted at a temperature range of from 250° C. to 550° C., and at atmospheric pressure with a space-time corresponding to the ratio of multimetallic mixed oxide solid catalyst mass to inlet molar flow rate of ethane (W/F°$_{ethane}$) in a range of from 10 $g_{cat}h(mol)^{-1}$ to 800 $g_{cat}h(mol)^{-1}$ to achieve an ethane conversion above 86 mol % and an ethylene selectivity above 95 mol % without formation of acetic acid and/or other oxygenated hydrocarbons.

14. The process of claim 1, wherein the oxidative dehydrogenation reaction is conducted at a reaction temperature range of from 250° C. to 550° C., under an operating pressure between 0.8 to 1 atm and a space-time corresponding to the ratio of multimetallic mixed oxide solid catalyst mass to inlet molar flow rate of ethane (W/F°$_{ethane}$) in a range of from $10g_{cat}h(mol)^{-1}$ to 800 $g_{cat}h(mol)^{-1}$ with an activated multimetallic mixed oxide solid catalyst supported on a metal oxide support to achieve ethylene selectivity above 95 mol %, and ethane conversion above 71 mol %.

* * * * *